United States Patent
Park et al.

(10) Patent No.: US 10,202,456 B2
(45) Date of Patent: Feb. 12, 2019

(54) METHOD FOR PRODUCING POLYPEPTIDES USING PDK-INACTIVATED CELLS

(71) Applicant: Samsung Bioepis Co., Ltd., Incheon (KR)

(72) Inventors: Eunyoung Park, Yongin-si (KR); Hye Young Suh, Seoul (KR); Hee Kyung Sung, Suwon-si (KR); Christina Yi, Seongnam-si (KR); Sunkyu Kim, Suwon-si (KR)

(73) Assignee: Samsung Bioepis Co., Ltd., Incheon (KR)

(*) Notice: Subject to any disclaimer, the term of this patent is extended or adjusted under 35 U.S.C. 154(b) by 50 days.

(21) Appl. No.: 14/929,623

(22) Filed: Nov. 2, 2015

(65) Prior Publication Data

US 2016/0130364 A1     May 12, 2016

(30) Foreign Application Priority Data

Oct. 31, 2014 (KR) .................. 10-2014-0150701

(51) Int. Cl.
| | |
|---|---|
| *C12N 9/12* | (2006.01) |
| *C12N 15/10* | (2006.01) |
| *C12N 15/09* | (2006.01) |
| *C07K 16/28* | (2006.01) |
| *C12P 21/02* | (2006.01) |
| *C12N 15/85* | (2006.01) |

(52) U.S. Cl.
CPC ............ *C07K 16/2863* (2013.01); *C12N 9/12* (2013.01); *C12P 21/02* (2013.01); *C12N 15/85* (2013.01)

(58) Field of Classification Search
CPC .......... C12N 9/12; C12N 15/09; C12N 15/102
See application file for complete search history.

(56) References Cited

U.S. PATENT DOCUMENTS

| | | | |
|---|---|---|---|
| 8,492,344 B2* | 7/2013 | Ostrov .................. | A61K 31/00 514/19.3 |
| 8,563,696 B2 | 10/2013 | Cheong et al. | |
| 8,637,286 B2 | 1/2014 | Burgard et al. | |
| 2011/0212507 A1 | 9/2011 | Burgard et al. | |
| 2013/0084605 A1 | 4/2013 | Zhou et al. | |

FOREIGN PATENT DOCUMENTS

| | | |
|---|---|---|
| EP | 1010755 B1 | 10/2010 |
| JP | 2000-232890 A | 8/2000 |
| KR | 2002-0017501 A | 9/2003 |
| KR | 2011-0047698 A | 5/2011 |
| WO | 2011/150241 A2 | 12/2011 |

OTHER PUBLICATIONS

Gudi et al., JBC, 270(48), 28989-28994, 1995.*
Zhou et al., Decreasing lactate level and increasing antibody production in Chinese Hamster Ovary cells (CHO) by reducing the expression of lactate dehydrogenase and pyruvate dehydrogenase kinases, *Journal of Biotechnology*, vol. 153: 27-34 (2011).

* cited by examiner

*Primary Examiner* — Maryam Monshipouri
(74) *Attorney, Agent, or Firm* — Leydig, Voit & Mayer, Ltd.

(57) ABSTRACT

Provided is a recombinant cell including inactivated pyruvate dehydrogenase kinase (PDK) gene, a composition for producing a polypeptide of interest including the recombinant cell, and a method of producing a polypeptide of interest using the recombinant cell.

19 Claims, 12 Drawing Sheets

Specification includes a Sequence Listing.

Genetic Elements Essential for Expression

FIG. 6

(2-8 mPDK1-1: SEQ ID NO: 24; PDK1: SEQ ID NO: 6; 2-8 mPDK1-2: SEQ ID NO: 25)

FIG. 7

(2-8 mPDK2-2: SEQ ID NO: 27; PDK2: SEQ ID NO: 8; 2-8 mPDK2-1: SEQ ID NO: 26)

(2-33 mPDK2: SEQ ID NO: 28; PDK2: SEQ ID NO: 8)

SEQUENCE LISTING

<160> NUMBER OF SEQ ID NOS: 35

<210> SEQ ID NO 1
<211> LENGTH: 460
<212> TYPE: PRT
<213> ORGANISM: Artificial Sequence
<220> FEATURE:
<223> OTHER INFORMATION: Synthetic (heavy chain of anti-c-Met antibody)

<400> SEQUENCE: 1

```
Met Glu Trp Ser Trp Val Phe Leu Val Thr Leu Leu Asn Gly Ile Gln
 1               5                  10                  15

Cys Glu Val Gln Leu Val Glu Ser Gly Gly Leu Val Gln Pro Gly
            20                  25                  30

Gly Ser Leu Arg Leu Ser Cys Ala Ala Ser Gly Phe Thr Phe Thr Asp
            35                  40                  45

Tyr Tyr Met Ser Trp Val Arg Gln Ala Pro Gly Lys Gly Leu Glu Trp
        50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400
```

```
Glu Asn Asn Tyr Lys Thr Thr Pro Pro Met Leu Asp Ser Asp Gly Ser
            405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
    450                 455                 460

<210> SEQ ID NO 2
<211> LENGTH: 1404
<212> TYPE: DNA
<213> ORGANISM: Artificial Sequence
<220> FEATURE:
<223> OTHER INFORMATION: Synthetic (polynucleotide encoding heavy chain
      of anti-c-Met antibody)

<400> SEQUENCE: 2
gaattcgccg ccaccatgga atggagctgg gttttctcg taacactttt aaatggtatc       60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg gtttttatta gaaacaaagc taatggttac     240
acaacagagt acagtgcatc tgtgaagggt cgtttcacta agcagagaa taattccaaa      300 aacacactgt acctgcagat gaacagcctg cgtgctgagg acactgccgt ctattattgt     360
gctagagata ctggtttgc ttactgggc aagggactc tggtcaccgt ctcctcggct        420
agcaccaagg gcccatcggt cttccccctg gcgccctgct ccaggagcac ctccgagagc     480
acagcggccc tgggctgcct ggtcaaggac tacttcccg aaccggtgac ggtgtcgtgg      540
aactcaggcg ctctgaccag cggcgtgcac accttccag ctgtcctaca gtcctcagga     600
ctctactccc tcagcagcgt ggtgaccgtg ccctccagca acttcggcac ccagacctac     660
acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc     780
ttccccccaa aacccaagga caccctcatg atctcccgga cccctgaggt cacgtgcgtg    840
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag   1020
gtctccaaca aaggcctccc agcccccatc gagaaaacca tctccaaaac caaagggcag   1080
ccccgagaac acaggtgta cccctgcccc catcccggg aggagatgac caagaaccag      1140
gtcagcctga cctgcctggt caaaggcttc taccccagcg acatcgccgt ggagtgggag   1200
agcaatgggc agccggagaa caactacaag accacgcctc ccatgctgga ctccgacggc   1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc   1380
ctgtctccgg gtaaatgact cgag                                          1404

<210> SEQ ID NO 3
<211> LENGTH: 240
<212> TYPE: PRT
<213> ORGANISM: Artificial Sequence
<220> FEATURE:
<223> OTHER INFORMATION: Synthetic (light chain of anti-c-Met antibody)
```

<400> SEQUENCE: 3

```
Met Asp Ser Gln Ala Gln Val Leu Met Leu Leu Leu Ser Val Ser
 1               5                  10                  15

Gly Thr Cys Gly Asp Ile Gln Met Thr Gln Ser Pro Ser Ser Leu Ser
             20                  25                  30

Ala Ser Val Gly Asp Arg Val Thr Ile Thr Cys Lys Ser Gln Ser
         35                  40                  45

Leu Leu Ala Ser Gly Asn Gln Asn Asn Tyr Leu Ala Trp Tyr Gln Gln
     50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
             85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
            115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 4
<211> LENGTH: 758
<212> TYPE: DNA
<213> ORGANISM: Artificial Sequence
<220> FEATURE:
<223> OTHER INFORMATION: Synthetic polynucleotide encoding polypeptide consisting of light chain of huAbF46-H4-A1(H36Y) and human kappa constant region

<400> SEQUENCE: 4

```
aattcactag tgattaattc gccgccacca tggattcaca ggcccaggtc ctcatgttgc      60
tgctgctatc ggtatctggt acctgtggag atatccagat gacccagtcc ccgagctccc     120
tgtccgcctc tgtgggcgat agggtcacca tcacctgcaa gtccagtcag agtctttag     180 ctagtggcaa ccaaaataac tacttggcct ggtaccaaca gaaaccagga aaagctccga     240
aaatgctgat tatttgggca tccactaggg tatctggagt cccttctcgc ttctctggat     300
ccgggtctgg gacggatttc actctgacca tcagcagtct gcagccggaa gacttcgcaa     360
cttattactg tcagcagtcc tacagccgcc cgtacacgtt cggacagggt accaaggtgg     420
agatcaaacg tacggtggct gcaccatctg tcttcatctt cccgccatct gatgagcagt     480
tgaaatctgg aactgcctct gttgtgtgcc tgctgaataa cttctatccc agagaggcca     540 agtacagtg gaaggtggat aacgccctcc aatcgggtaa ctcccaggag agtgtcacag     600
```

| | |
|---|---|
| agcaggacag caaggacagc acctacagcc tcagcagcac cctgacgctg agcaaagcag | 660 |
| actacgagaa acacaaagtc tacgcctgcg aagtcaccca tcagggcctg agctcgcccg | 720 |
| tcacaaagag cttcaacagg ggagagtgtt gactcgag | 758 |

<210> SEQ ID NO 5
<211> LENGTH: 10281
<212> TYPE: DNA
<213> ORGANISM: Artificial Sequence
<220> FEATURE:
<223> OTHER INFORMATION: Synthetic (expression vector of anti-c-Met antibody)

<400> SEQUENCE: 5

| | |
|---|---|
| ggagaaaggc cttctgccga gtcattgtcc ttgtcccgcg gccccgggag cccccccgcga | 60 |
| ccggcctggg aggctcaggg aggttgaagg gggctgagca aaggaagccc cgtcattacc | 120 |
| tcaaatgtga cccaaaaata aagacccgtc catctcgcag ggtgggccag ggcgggtcag | 180 |
| gagggagggg agggagaccc cgactctgca gaaggcgctc gctgcgtgcc ccacgtccgc | 240 |
| cgaacgcggg gttcgcgacc cgaggggacc gcggggctg aggggagggg ccgcggagcc | 300 |
| gcggctaagg aacgcgggcc gcccacccgc tcccggtgca gcggcctccg cgccgggttt | 360 |
| tggcgcctcc cgcgggcgcc ccctcctca cggcgagcgc tgccacgtca gacgaagggc | 420 |
| gcagcgagcg tcctgatcct tccgcccgga cgctcaggac agcggcccgc tgctcataag | 480 |
| actcggcctt agaaccccag tatcagcaga aggacatttt aggacgggac ttgggtgact | 540 |
| ctagggcact ggttttcttt ccagagagcg gaacaggcga ggaaaagtag tcccttctcg | 600 |
| gcgattctgc ggagggatct ccgtggggcg gtgaacgccg atgattatat aaggacgcgc | 660 |
| cgggtgtggc acagctagtt ccgtcgcagc cgggatttgg gtcgcagttc ttgtttgtgg | 720 |
| atcgctgtga tcgtcacttg gtgagtagcg ggctgctggg ctggccgggg ctttcgtggc | 780 |
| cgccgggccg ctcggtggga cggaggcgtg tggagagacc gccaagggct gtagtctggg | 840 |
| tccgcgagca aggttgccct gaactggggg ttgggggag cgcagcaaaa tggcggctgt | 900 |
| tcccgagtct tgaatggaag acgcttgtga ggcgggctgt gaggtcgttg aaacaaggtg | 960 |
| gggggcatgg tgggcggcaa gaacccaagg tcttgaggcc ttcgctaatg cgggaaagct | 1020 |
| cttattcggg tgagatgggc tggggcacca tctggggacc ctgacgtgaa gtttgtcact | 1080 |
| gactggagaa ctcggtttgt cgtctgttgc gggggcggca gttatggcgg tgccgttggg | 1140 |
| cagtgcaccc gtacctttgg gagcgcgcgc cctcgtcgtg tcgtgacgtc accgttctg | 1200 |
| ttggcttata atgcagggtg gggccacctg ccggtaggtg tgcggtaggc ttttctccgt | 1260 |
| cgcaggacgc agggttcggg cctagggtag gctctcctga atcgacaggc gccgacctc | 1320 |
| tggtgagggg agggataagt gaggcgtcag tttctctggt cggttttatg tacctatctt | 1380 |
| cttaagtagc tgaagctccg gttttgaact atgcgctcgg ggttggcgag tgtgttttgt | 1440 |
| gaagtttttt aggcacccttt tgaaatgtaa tcatttgggt caatatgtaa ttttcagtgt | 1500 |
| tagactagta aattgtccgc taaattctgg ccgttttgg cttttttgtt agacgaattg | 1560 |
| gtgagaatat ttagaaaaag ctaaaactaa ttctttgaac cattaatttt cttaattagg | 1620 |
| aacctggcac catatggaac ttggcttgtt tttaaatgtg attttttttt aagtaatgcg | 1680 |
| tattctttca tcttgtgcta ctagattagt ggtgatttca ttaagcagat gcttatattg | 1740 |
| tgctaatgtt tgctgtatgt tttcaggaat tcactagtga ttaattcgcc gccaccatgg | 1800 |
| actcccaggc ccaggtgctg atgctcctgc tgctgtccgt gtccggcacc tgtggcgaca | 1860 |

```
tccagatgac ccagtcccca tccagcctga gcgcttccgt gggcgacaga gtgaccatca    1920
catgcaagtc ctcccagtcc ctgctggcct ccggcaacca gaacaactac ctggcctggt    1980
atcagcagaa gcccggcaag ccccccaaga tgctgatcat ctgggcctcc accagagtgt    2040
ccggcgtgcc ctccagattc tccggctctg gctccggcac cgacttcacc ctgaccatct    2100
ccagcctgca gcccgaggac ttcgccacct actactgcca gcagtcctac tcccggccct    2160
acaccttcgg ccagggcacc aaggtggaaa tcaagcgtac ggtggccgct ccctccgtgt    2220
tcatcttccc accctccgac gagcagctga agtccggcac cgcctccgtc gtgtgcctgc    2280
tgaacaactt ctaccccgc gaggccaagg tgcagtggaa ggtggacaac gccctgcagt     2340
ccggcaactc ccaggaatcc gtcaccgagc aggactccaa ggacagcacc tactccctgt    2400
cctccaccct gaccctgtcc aaggccgact acgagaagca caaggtgtac gcctgcgaag    2460
tgacccacca gggcctgtcc agccccgtga ccaagtcctt caaccggggc gagtgctgac    2520
tcgagaaact gtgccttcta gttgccagcc atctgttgtt tgcccctccc ccgtgccttc    2580
cttgaccctg gaaggtgcca ctcccactgt cctttcctaa taaaatgagg aaattgcatc    2640
gcattgtctg agtaggtgtc attctattct ggggggtggg gtgggcagg acagcaaggg     2700 ggaggattgg gaagacaata gcaggcatgc tggggatgcg gtgggctcta tgggatatcg    2760
gagaaggcgc gtggagaaag gccttctgcc gagtcattgt ccttgtcccg cggcccggg     2820 agcccccgc gaccggcctg ggaggctcag ggaggttgaa gggggctgag caaaggaagc     2880
cccgtcatta cctcaaatgt gacccaaaaa taaagacccg tccatctcgc agggtgggcc    2940
agggcgggtc aggagggagg ggagggagac cccgactctg cagaaggcgc tcgctgcgtg    3000
ccccacgtcc gccgaacgcg gggttcgcga cccgagggga ccgcggggc tgaggggagg     3060 ggccgcggag ccgcggctaa ggaacgcggg ccgcccaccc gctcccggtg cagcggcctc    3120
cgcgccgggt tttggcgcct cccgcggcg cccccctcct cacggcgagc gctgccacgt     3180
cagacgaagg gcgcagcgag cgtcctgatc cttccgcccg gacgctcagg acagcggccc    3240
gctgctcata agactcggcc ttagaacccc agtatcagca gaaggacatt ttaggacggg    3300
acttgggtga ctctagggca ctggttttct ttccagagag cggaacaggc gaggaaaagt    3360
agtcccttct cggcgattct gcggagggat ctccgtgggg cggtgaacgc cgatgattat    3420
ataaggacgc gccgggtgtg gcacagctag ttccgtcgca gccgggattt gggtcgcagt    3480
tcttgtttgt ggatcgctgt gatcgtcact tggtgagtag cgggctgctg ggctggccgg    3540
ggctttcgtg gccgccgggc cgctcggtgg gacggaggcg tgtggagaga ccgccaaggg    3600
ctgtagtctg ggtccgcgag caaggttgcc ctgaactggg ggttgggggg agcgcagcaa    3660
aatggcggct gttcccgagt cttgaatgga agacgcttgt gaggcgggct gtgaggtcgt    3720
tgaaacaagg tgggggcat ggtgggcggc aagaacccaa ggtcttgagg ccttcgctaa     3780
tgcgggaaag ctcttattcg ggtgagatgg gctgggcac catctgggga ccctgacgtg     3840
aagtttgtca ctgactggag aactcggttt gtcgtctgtt gcggggcgg cagttatggc     3900 ggtgccgttg gcagtgcac ccgtaccttt gggagcgcgc gccctcgtcg tgtcgtgacg     3960
tcacccgttc tgttggctta taatgcaggg tggggccacc tgccggtagg tgtgcggtag    4020
gcttttctcc gtcgcaggac gcagggttcg ggcctagggt aggctctcct gaatcgacag    4080
gcgccggacc tctggtgagg ggagggataa gtgaggcgtc agtttctctg gtcggttta     4140 tgtacctatc ttcttaagta gctgaagctc cggttttgaa ctatgcgctc ggggttggcg    4200
```

-continued

```
agtgtgtttt gtgaagtttt ttaggcacct tttgaaatgt aatcatttgg gtcaatatgt    4260
aattttcagt gttagactag taaattgtcc gctaaattct ggccgttttt ggctttttttg   4320 ttagacgaat tggtgagaat atttagaaaa agctaaaact aattctttga accattaatt    4380
ttcttaatta ggaacctggc accatatgga acttggcttg tttttaaatg tgattttttt    4440
ttaagtaatg cgtattcttt catcttgtgc tactagatta gtggtgattt cattaagcag    4500
atgcttatat tgtgctaatg tttgctgtat gttttcagga attcgccgcc accatggaat    4560
ggtcctgggt gttcctggtc accctgctga acggcatcca gtgcgaggtg cagctggtgg    4620
aatccggcgg aggactggtg cagcctggcg gctccctgag actgtcttgc gccgcctccg    4680
gcttcacctt caccgactac tacatgtcct gggtccgaca ggcccctggc aagggcctgg    4740
aatggctggg cttcatccgg aacaaggcca acgctacac caccgagtac tccgcctccg     4800
tgaagggccg gttcaccatc tcccgggaca actccaagaa cacactgtac ctgcagatga    4860
actccctgcg ggccgaggac accgccgtgt actactgcgc cagagacaat tggttcgcct    4920
actggggcca gggcaccctg gtcaccgtgt cctctgctag caccaagggc cctccgtgt     4980 tccctctggc cccttgctcc cggtccacct ccgagtctac cgccgctctg ggctgcctgg    5040
tcaaggacta cttccccgag cccgtgaccg tgtcctggaa ctctggcgcc ctgacctccg    5100
gcgtgcacac cttccctgcc gtgctgcagt cctccggcct gtactccctg tcctccgtcg    5160
tgaccgtgcc ctcctccaac ttcggcaccc agacctacac ctgtaacgtg gaccacaagc    5220
cctccaacac caaggtggac aagaccgtgg aacggaagtg ctgcgtggaa tgccccccct    5280
gccctgctcc tcctgtggca ggccctagcg tgttcctgtt ccccccaaag cccaaggaca    5340
ccctgatgat ctcccggacc cccgaagtga cctgcgtggt ggtggacgtg tcccacgagg    5400
accccgaggt gcagttcaat tggtacgtgg acggcgtgga agtgcacaac gccaagacca    5460
agcccagaga ggaacagttc aactccacct tccgggtggt gtccgtgctg accgtggtgc    5520
accaggactg gctgaacggc aaagagtaca agtgcaaggt gtccaacaag gcctgcctg     5580 cccccatcga aaagaccatc agcaagacca agggccagcc ccgcgagccc caggtgtaca    5640
cactgccccc tagccgggaa gagatgacca agaaccaggt gtccctgacc tgtctcgtca    5700
aaggcttcta ccccctccgat atcgccgtgg aatgggagtc caacggccag cccgagaaca    5760
actacaagac cacccccccc atgctggact ccgacggctc attcttcctg tactccaagc    5820
tgacagtgga caagtcccgg tggcagcagg gcaacgtgtt ctcctgctcc gtgatgcacg    5880
aggccctgca caaccactac acccagaagt ccctgtccct gagccccggc aagtgactcg    5940
agggagaagc ggccgcaaag ccgcccctct ccctcccccc ccctaacgt tactggccga    6000 agccgcttgg aataaggccg gtgtgcgttt gtctatatgt tattttccac catattgccg    6060
tcttttggca atgtgagggc ccggaaacct ggccctgtct tcttgacgag cattcctagg    6120
ggtctttccc ctctcgccaa aggaatgcaa ggtctgttga atgtcgtgaa ggaagcagtt    6180
cctctggaag cttcttgaag acaaacaacg tctgtagcga ccctttgcag gcagcggaac    6240
cccccacctg gcgacaggtg cctctgcggc caaaagccac gtgtataaga tacacctgca    6300
aaggcggcac aaccccagtg ccacgttgtg agttggatag ttgtggaaag agtcaaatgg    6360
ctctcctcaa gcgtattcaa caaggggctg aaggatgccc agaaggtacc ccattgtatg    6420
ggatctgatc tggggcctcg gtacacatgc tttacatgtg tttagtcgag gttaaaaaaa    6480
cgtctaggcc ccccgaacca cggggacgtg gttttccttt gaaaaacacg atgataatat    6540
ggccacaaaa agatctgcca ccatggccac ctcagcaagt tcccacttga acaaaaacat    6600
```

```
caagcaaatg tacttgtgcc tgccccaggg tgagaaagtc caagccatgt atatctgggt   6660
tgatggtact ggagaaggac tgcgctgcaa aacccgcacc ctggactgtg agcccaagtg   6720
tgtagaagag ttacctgagt ggaattttga tggctctagt acctttcagt ctgagggctc   6780
caacagtgac atgtatctca gccctgttgc catgtttcgg gacccttcc gcagagatcc    6840 caacaagctg gtgttctgtg aagttttcaa gtacaaccgg aagcctgcag agaccaattt   6900
aaggcactcg tgtaaacgga taatggacat ggtgagcaac cagcacccct ggtttggaat   6960
ggaacaggag tatactctga tgggaacaga tgggcaccct tttggttggc cttccaatgg   7020
ctttcctggg ccccaaggtc cgtattactg tggtgtgggc gcagacaaag cctatggcag   7080
ggatatcgtg gaggctcact accgcgcctg cttgtatgct ggggtcaaga ttacaggaac   7140
aaatgctgag gtcatgcctg cccagtggga attccaaata ggaccctgtg aaggaatccg   7200
catgggagat catctctggg tggcccgttt catcttgcat cgagtatgtg aagactttgg   7260
ggtaatagca acctttgacc ccaagcccat tcctgggaac tggaatggtg caggctgcca   7320
taccaacttt agcaccaagg ccatgcggga ggagaatggt ctgaagcaca tcgaggaggc   7380
catcgagaaa ctaagcaagc ggcaccggta ccacattcga gcctacgatc ccaaggggg   7440 cctggacaat gcccgtcgtc tgactgggtt ccacgaaacg tccaacatca acgactttc   7500 tgctggtgtc gccaatcgca gtgccagcat ccgcattccc cggactgtcg gccaggagaa   7560
gaaaggttac tttgaagacc gccgcccctc tgccaattgt gaccccttg cagtgacaga    7620 agccatcgtc cgcacatgcc ttctcaatga gactggcgac cagcccttcc aatacaaaaa   7680
ctaaggccgg ccaaagtcga gaaactgtgc cttctagttg ccagccatct gttgtttgcc   7740 cctccccgt gccttccttg accctggaag gtgccactcc cactgtcctt tcctaataaa    7800
atgaggaaat tgcatcgcat tgtctgagta ggtgtcattc tattctgggg ggtggggtgg   7860
ggcaggacag caaggggag gattgggaag acaatagcag gcatgctggg gatgcggtgg    7920
gctctatggg atatcggaga aggcgcgccg ctgcctcgcg cgtttcggtg atgacggtga   7980
aaacctctga cacatgcagc tcccggagac ggtcacagct tgtctgtaag cggatgccgg   8040
gagcagacaa gcccgtcagg gcgcgtcagc gggtgttggc gggtgtcggg gcgcagccat   8100
gacccagtca cgtagcgata gcggagtgta tactggctta actatgcggc atcagagcag   8160
attgtactga gagtgcacca tatgcggtgt gaaataccgc acagatgcgt aaggagaaaa   8220
taccgcatca ggcgctcttc cgcttcctcg ctcactgact cgctgcgctc ggtcgttcgg   8280
ctgcggcgag cggtatcagc tcactcaaag gcggtaatac ggttatccac agaatcaggg   8340
gataacgcag gaaagaacat gtgagcaaaa ggccagcaaa aggccaggaa ccgtaaaaag   8400
gccgcgttgc tggcgttttt ccataggctc cgcccccctg acgagcatca aaaaatcga    8460 cgctcaagtc agaggtggcg aaacccgaca ggactataaa gataccaggc gtttccccct   8520
ggaagctccc tcgtgcgctc tcctgttccg accctgccgc ttaccggata cctgtccgcc   8580
tttctccctt cggaagcgt ggcgctttct catagctcac gctgtaggta tctcagttcg    8640
gtgtaggtcg ttcgctccaa gctgggctgt gtgcacgaac cccccgttca gcccgaccgc   8700
tgcgccttat ccggtaacta tcgtcttgag tccaacccgg taagacacga cttatcgcca   8760
ctggcagcag ccactggtaa caggattagc agagcgaggt atgtaggcgg tgctacagag   8820
ttcttgaagt ggtggcctaa ctacggctac actagaagga cagtatttgg tatctgcgct   8880
ctgctgaagc cagttacctt cggaaaaaga gttggtagct cttgatccgg caaacaaacc   8940
```

| | |
|---|---:|
| accgctggta gcggtggttt ttttgtttgc aagcagcaga ttacgcgcag aaaaaaagga | 9000 |
| tctcaagaag atcctttgat cttttctacg gggtctgacg ctcagtggaa cgaaaactca | 9060 |
| cgttaaggga ttttggtcat gagattatca aaaggatct tcacctagat ccttttaaat | 9120 |
| taaaaatgaa gttttaaatc aatctaaagt atatatgagt aaacttggtc tgacagttac | 9180 |
| caatgcttaa tcagtgaggc acctatctca gcgatctgtc tatttcgttc atccatagtt | 9240 |
| gcctgactcc ccgtcgtgta gataactacg atacgggagg gcttaccatc tggccccagt | 9300 |
| gctgcaatga taccgcgaga cccacgctca ccggctccag atttatcagc aataaaccag | 9360 |
| ccagccggaa gggccgagcg cagaagtggt cctgcaactt tatccgcctc catccagtct | 9420 |
| attaattgtt gccgggaagc tagagtaagt agttcgccag ttaatagttt gcgcaacgtt | 9480 |
| gttgccattg ctgcaggcat cgtggtgtca cgctcgtcgt ttggtatggc ttcattcagc | 9540 |
| tccggttccc aacgatcaag gcgagttaca tgatccccca tgttgtgcaa aaaagcggtt | 9600 |
| agctccttcg gtcctccgat cgttgtcaga agtaagttgg ccgcagtgtt atcactcatg | 9660 |
| gttatggcag cactgcataa ttctcttact gtcatgccat ccgtaagatg cttttctgtg | 9720 |
| actggtgagt actcaaccaa gtcattctga aatagtgta tgcggcgacc gagttgctct | 9780 |
| tgcccggcgt caacacggga taataccgcg ccacatagca gaactttaaa agtgctcatc | 9840 |
| attggaaaac gttcttcggg gcgaaaactc tcaaggatct taccgctgtt gagatccagt | 9900 |
| tcgatgtaac ccactcgtgc acccaactga tcttcagcat cttttacttt caccagcgtt | 9960 |
| tctgggtgag caaaaacagg aaggcaaaat gccgcaaaaa agggaataag ggcgacacgg | 10020 |
| aaatgttgaa tactcatact cttcctttt caatattatt gaagcattta tcagggttat | 10080 |
| tgtctcatga gcggatacat atttgaatgt atttagaaaa ataaacaaat aggggttccg | 10140 |
| cgcacatttc cccgaaaagt gccacctgac gtctaagaaa ccattattat catgacatta | 10200 |
| acctataaaa ataggcgtat cacgaggccc tttcgtcttc aagaaagtta cgctagggat | 10260 |
| aacagggtaa tatagacgcg t | 10281 |

<210> SEQ ID NO 6
<211> LENGTH: 1077
<212> TYPE: DNA
<213> ORGANISM: Artificial Sequence
<220> FEATURE:
<223> OTHER INFORMATION: Synthetic PDK1 gene

<400> SEQUENCE: 6

| | |
|---|---:|
| atgtttcttc gacaagagtt gcctgttaga ttggcaaata taatgaaaga ataagccttt | 60 |
| cttccagaca atcttctcag gacgccatca gtacagttgg tacaaagttg gtatatacag | 120 |
| agtcttcagg agctgcttga ttttaaggac aaaagtgctg aagatgctaa aactatttat | 180 |
| gaattcacag acacagtgat aaggatcaga aaccggcaca atgatgtcat tccaaccatg | 240 |
| gcccagggtg tgaccgaata caaggagagc ttcggggtgg atcctgtcac cagccaaaat | 300 |
| gtccagtact ttttggatcg attctacatg agtcgcattt caattagaat gttactcaac | 360 |
| cagcactctt tattgtttgg tggaaaagga agcccatctc atcgaaaaca cattggaagc | 420 |
| ataaatccaa actgcgatgt agtcgaagtc attaaagatg gctatgaaaa tgctaggcgg | 480 |
| ctttgtgatt tgtattatgt taactctcct gaactagaac ttgaagaact aaatgcgatt | 540 |
| tcaccaggac agacaatacag agtggtttat gtaccatccc atctctatca catggtgttt | 600 |
| gaactgttca gaatgcaat gagggctacc atggagcacc atgctgacaa ggtgtctat | 660 |
| cccccgattc aagttcatgt cacactgggt gaggaggatt tgactgtgaa gatgagtgac | 720 |

```
cggggaggtg gtgttccact gagaaagatt gacagactct tcaactacat gtactcaact    780
gcaccccggc ctcgttttga dacatcccgt gcagtgcccc tggctggttt tggttatgga    840
ttgcccatat cacgcctcta tgcacagtac ttccagggg acctaaagct gtactccttg     900
gagggctacg ggactgacgc tgttatctat attaaggctc tgtcaacaga atccatcgag    960
agactccccg tgtataataa agctgcctgg aagcattaca aaaccaacca tgaagctgac   1020
gactggtgtg tccccagcag agagccgaaa gacatgacca cattccgaag ctcttag     1077
```

<210> SEQ ID NO 7
<211> LENGTH: 358
<212> TYPE: PRT
<213> ORGANISM: Artificial Sequence
<220> FEATURE:
<223> OTHER INFORMATION: Synthetic PDK1 protein

<400> SEQUENCE: 7

```
Met Phe Leu Arg Gln Glu Leu Pro Val Arg Leu Ala Asn Ile Met Lys
 1               5                  10                  15

Glu Ile Ser Leu Leu Pro Asp Asn Leu Leu Arg Thr Pro Ser Val Gln
            20                  25                  30

Leu Val Gln Ser Trp Tyr Ile Gln Ser Leu Gln Glu Leu Leu Asp Phe
        35                  40                  45

Lys Asp Lys Ser Ala Glu Asp Ala Lys Thr Ile Tyr Glu Phe Thr Asp
    50                  55                  60

Thr Val Ile Arg Ile Arg Asn Arg His Asn Asp Val Ile Pro Thr Met
65                  70                  75                  80

Ala Gln Gly Val Thr Glu Tyr Lys Glu Ser Phe Gly Val Asp Pro Val
                85                  90                  95

Thr Ser Gln Asn Val Gln Tyr Phe Leu Asp Arg Phe Tyr Met Ser Arg
            100                 105                 110

Ile Ser Ile Arg Met Leu Leu Asn Gln His Ser Leu Leu Phe Gly Gly
        115                 120                 125

Lys Gly Ser Pro Ser His Arg Lys His Ile Gly Ser Ile Asn Pro Asn
    130                 135                 140

Cys Asp Val Val Glu Val Ile Lys Asp Gly Tyr Glu Asn Ala Arg Arg
145                 150                 155                 160

Leu Cys Asp Leu Tyr Tyr Val Asn Ser Pro Glu Leu Glu Leu Glu Glu
                165                 170                 175

Leu Asn Ala Ile Ser Pro Gly Gln Thr Ile Gln Val Val Tyr Val Pro
            180                 185                 190

Ser His Leu Tyr His Met Val Phe Glu Leu Phe Lys Asn Ala Met Arg
        195                 200                 205

Ala Thr Met Glu His His Ala Asp Lys Gly Val Tyr Pro Pro Ile Gln
    210                 215                 220

Val His Val Thr Leu Gly Glu Glu Asp Leu Thr Val Lys Met Ser Asp
225                 230                 235                 240

Arg Gly Gly Gly Val Pro Leu Arg Lys Ile Asp Arg Leu Phe Asn Tyr
                245                 250                 255

Met Tyr Ser Thr Ala Pro Arg Pro Arg Phe Glu Thr Ser Arg Ala Val
            260                 265                 270

Pro Leu Ala Gly Phe Gly Tyr Gly Leu Pro Ile Ser Arg Leu Tyr Ala
        275                 280                 285

Gln Tyr Phe Gln Gly Asp Leu Lys Leu Tyr Ser Leu Glu Gly Tyr Gly
    290                 295                 300
```

Thr Asp Ala Val Ile Tyr Ile Lys Ala Leu Ser Thr Glu Ser Ile Glu
305                 310                 315                 320

Arg Leu Pro Val Tyr Asn Lys Ala Ala Trp Lys His Tyr Lys Thr Asn
                325                 330                 335

His Glu Ala Asp Asp Trp Cys Val Pro Ser Arg Glu Pro Lys Asp Met
            340                 345                 350

Thr Thr Phe Arg Ser Ser
        355

<210> SEQ ID NO 8
<211> LENGTH: 1224
<212> TYPE: DNA
<213> ORGANISM: Artificial Sequence
<220> FEATURE:
<223> OTHER INFORMATION: Synthetic PDK2 gene

<400> SEQUENCE: 8

| | | | | | |
|---|---|---|---|---|---|
| atgcgctgga | tccgggcact | gttgaagaat | gcgtccctag | caggggcgcc | caagtacatc | 60 |
| gagcacttca | gcaagttctc | cccgtccccg | ctgtccatga | agcagtttct | agacttcgga | 120 |
| tccagcaatg | cctgcgagaa | aacttccttc | accttcctta | ggcaggagct | gcctgtgcgc | 180 |
| ctggccaaca | tcatgaaaga | gattaacttg | cttcccgaca | gagtgctggg | cacccctca | 240 |
| gtgcagctgg | tgcagagctg | gtatgtccag | agtctgctgg | acatcatgga | attcctggac | 300 |
| aaggatccag | aggatcaccg | gacactaagc | cagttcaccg | atgccctggt | caccatccgg | 360 |
| aaccggcaca | tgacgtagt | gcccaccatg | gcacagggag | tgctggagta | caaggacacc | 420 |
| tatggcgatg | acccggtgtc | caaccagaac | attcagtact | tcttggaccg | cttctacctc | 480 |
| agccggatct | ccatccgcat | gctcatcaac | cagcacaccc | tcatctttga | tggaagtacc | 540 |
| aacccagctc | accccaaaca | cattggcagc | attgacccta | actgcagcgt | gtctgatgtg | 600 |
| gtaaaagatg | cctatgacat | ggccaagctc | ctgtgtgaca | atactacat | ggcttcacct | 660 |
| gatctagaga | tccaggaagt | taatgccacc | aatgccaacc | agcccattca | catggtctac | 720 |
| gtccctcc | acctctacca | catgctcttt | gagctcttca | gaatgccat | gcgggccacg | 780 |
| gtggagagcc | acgagtccag | cctcaccctc | cctcctatca | agattatggt | agccttgggt | 840 |
| gaagaagatc | tgtccatcaa | aatgagtgac | cgaggtgggg | gtgtcccctt | gaggaagatt | 900 |
| gagaggctct | tcagctacat | gtactccaca | gcccccacac | cccagcctgg | cactgggggt | 960 |
| accccactgg | ctggctttgg | gtatggactc | cccatttccc | gcctctacgc | caagtacttc | 1020 |
| caaggagact | tgcagctctt | ctctatggag | ggctttggga | cagatgctgt | catatatctc | 1080 |
| aaggccctgt | ccacggactc | agtggagcgt | ctgcctgtct | acaacaagtc | tgcctggcgc | 1140 |
| cactaccaga | ccatccagga | ggccggtgac | tggtgtgtgc | ccagcacgga | gcccaagaac | 1200 |
| acatccacgt | atcgggtcag | ctag | | | | 1224 |

<210> SEQ ID NO 9
<211> LENGTH: 407
<212> TYPE: PRT
<213> ORGANISM: Artificial Sequence
<220> FEATURE:
<223> OTHER INFORMATION: Synthetic PDK2 protein

<400> SEQUENCE: 9

Met Arg Trp Ile Arg Ala Leu Leu Lys Asn Ala Ser Leu Ala Gly Ala
1               5                   10                  15

Pro Lys Tyr Ile Glu His Phe Ser Lys Phe Ser Pro Ser Pro Leu Ser

```
                    20                  25                  30
Met Lys Gln Phe Leu Asp Phe Gly Ser Ser Asn Ala Cys Glu Lys Thr
            35                  40                  45

Ser Phe Thr Phe Leu Arg Gln Glu Leu Pro Val Arg Leu Ala Asn Ile
 50                  55                  60

Met Lys Glu Ile Asn Leu Leu Pro Asp Arg Val Leu Gly Thr Pro Ser
 65                  70                  75                  80

Val Gln Leu Val Gln Ser Trp Tyr Val Gln Ser Leu Leu Asp Ile Met
                85                  90                  95

Glu Phe Leu Asp Lys Asp Pro Glu Asp His Arg Thr Leu Ser Gln Phe
            100                 105                 110

Thr Asp Ala Leu Val Thr Ile Arg Asn Arg His Asn Asp Val Val Pro
        115                 120                 125

Thr Met Ala Gln Gly Val Leu Glu Tyr Lys Asp Thr Tyr Gly Asp Asp
    130                 135                 140

Pro Val Ser Asn Gln Asn Ile Gln Tyr Phe Leu Asp Arg Phe Tyr Leu
145                 150                 155                 160

Ser Arg Ile Ser Ile Arg Met Leu Ile Asn Gln His Thr Leu Ile Phe
                165                 170                 175

Asp Gly Ser Thr Asn Pro Ala His Pro Lys His Ile Gly Ser Ile Asp
            180                 185                 190

Pro Asn Cys Ser Val Ser Asp Val Val Lys Asp Ala Tyr Asp Met Ala
        195                 200                 205

Lys Leu Leu Cys Asp Lys Tyr Tyr Met Ala Ser Pro Asp Leu Glu Ile
    210                 215                 220

Gln Glu Val Asn Ala Thr Asn Ala Asn Gln Pro Ile His Met Val Tyr
225                 230                 235                 240

Val Pro Ser His Leu Tyr His Met Leu Phe Glu Leu Phe Lys Asn Ala
                245                 250                 255

Met Arg Ala Thr Val Glu Ser His Glu Ser Ser Leu Thr Leu Pro Pro
            260                 265                 270

Ile Lys Ile Met Val Ala Leu Gly Glu Glu Asp Leu Ser Ile Lys Met
        275                 280                 285

Ser Asp Arg Gly Gly Val Pro Leu Arg Lys Ile Glu Arg Leu Phe
    290                 295                 300

Ser Tyr Met Tyr Ser Thr Ala Pro Thr Pro Gln Pro Gly Thr Gly Gly
305                 310                 315                 320

Thr Pro Leu Ala Gly Phe Gly Tyr Gly Leu Pro Ile Ser Arg Leu Tyr
                325                 330                 335

Ala Lys Tyr Phe Gln Gly Asp Leu Gln Leu Phe Ser Met Glu Gly Phe
            340                 345                 350

Gly Thr Asp Ala Val Ile Tyr Leu Lys Ala Leu Ser Thr Asp Ser Val
        355                 360                 365

Glu Arg Leu Pro Val Tyr Asn Lys Ser Ala Trp Arg His Tyr Gln Thr
    370                 375                 380

Ile Gln Glu Ala Gly Asp Trp Cys Val Pro Ser Thr Glu Pro Lys Asn
385                 390                 395                 400

Thr Ser Thr Tyr Arg Val Ser
                405

<210> SEQ ID NO 10
<211> LENGTH: 1248
<212> TYPE: DNA
<213> ORGANISM: Artificial Sequence
```

<220> FEATURE:
<223> OTHER INFORMATION: Synthetic PDK3 gene

<400> SEQUENCE: 10

```
atgcggctct tctttaggct gctcaagcag ccggtgccca acagatcga gcgctactcc      60
cgcttctctc cgtctccgct ctctatcaaa cagttcttgg acttcggaag agataatgca    120
tgtgaaaaaa cttcatatat gtttctgcgc aaggagcttc ctgtacgact ggcgaacaca    180
atgagagaag ttaatctttt gccggataac ttgttgaacc gcccttcagt gggattagtt    240
cagagttggt acatgcagag cttttcttga cttttagaat atgaaaacaa gagcccagaa    300
gacccacggg tttagataa ctttctccat gtttttgatta atatcagaaa cagacacaac    360
gatgttgttc ccacaatggc ccaaggcgtg attgagtaca agaaaagtt cggatttgat    420
ccatttatta gcagtaacat ccagtatttc ctggatcgtt tttataccaa ccgcatctct    480
ttccgaatgc ttattaacca acacacactt ctgtttggtg gtgacactaa tcctgctcat    540
cctaagcaca tagggagtat cgatcccacc tgtaatgtag ctgatgtcgt gaaagatgca    600
tatgaaacag ctaagctact ctgtgaacag tattacctgg tagctccaga gctggaagtg    660
gaagaattca atgccaaagc accaaacaaa cctattcagg tggtttatgt gccgtctcat    720
ctgtttcaca tgctatttga gctgttcaag aactcgatga gagcaacagt tgaactacat    780
gaaaatagaa aagaggggcta cccagctgtt aaaactctcg ttactcttgg taaagaagac    840
ttgtccatta agataagtga cttaggtggt ggagtcccac ttcgaaaaat agaccgtctt    900
tttaactaca tgtattccac tgctcctcga cccagcctgg agcctacaag agctgctccc    960
ttggctggat ttggttatgg cttgccaatt tctcgactgt atgccagata ttttcaggga   1020
gatctaaaac tgtattccat ggaaggagtg gtaccgatg ctgttattta tctgaaggcc   1080
ctttcaagtg aatcatttga gggctgcccc gttttcaata gtctgcatg cgccattac   1140
aagacaactc ctgaagctga tgactggagc aatcccagta cgaaccaag ggatgcatca   1200
aaatacaagg ctaaacagga caagatcaag actaatagaa ctttgtag              1248
```

<210> SEQ ID NO 11
<211> LENGTH: 415
<212> TYPE: PRT
<213> ORGANISM: Artificial Sequence
<220> FEATURE:
<223> OTHER INFORMATION: Synthetic PDK3 protein

<400> SEQUENCE: 11

```
Met Arg Leu Phe Phe Arg Leu Leu Lys Gln Pro Val Pro Lys Gln Ile
  1               5                  10                  15

Glu Arg Tyr Ser Arg Phe Ser Pro Ser Pro Leu Ser Ile Lys Gln Phe
                 20                  25                  30

Leu Asp Phe Gly Arg Asp Asn Ala Cys Glu Lys Thr Ser Tyr Met Phe
             35                  40                  45

Leu Arg Lys Glu Leu Pro Val Arg Leu Ala Asn Thr Met Arg Glu Val
         50                  55                  60

Asn Leu Leu Pro Asp Asn Leu Leu Asn Arg Pro Ser Val Gly Leu Val
 65                  70                  75                  80

Gln Ser Trp Tyr Met Gln Ser Phe Leu Glu Leu Glu Tyr Glu Asn
                 85                  90                  95

Lys Ser Pro Glu Asp Pro Arg Val Leu Asp Asn Phe Leu His Val Leu
                100                 105                 110

Ile Asn Ile Arg Asn Arg His Asn Asp Val Val Pro Thr Met Ala Gln
```

```
                    115                 120                 125
Gly Val Ile Glu Tyr Lys Glu Lys Phe Gly Phe Asp Pro Phe Ile Ser
            130                 135                 140

Ser Asn Ile Gln Tyr Phe Leu Asp Arg Phe Tyr Thr Asn Arg Ile Ser
145                 150                 155                 160

Phe Arg Met Leu Ile Asn Gln His Thr Leu Phe Gly Gly Asp Thr
                165                 170                 175

Asn Pro Ala His Pro Lys His Ile Gly Ser Ile Asp Pro Thr Cys Asn
            180                 185                 190

Val Ala Asp Val Val Lys Asp Ala Tyr Glu Thr Ala Lys Leu Leu Cys
            195                 200                 205

Glu Gln Tyr Tyr Leu Val Ala Pro Glu Leu Glu Val Glu Glu Phe Asn
        210                 215                 220

Ala Lys Ala Pro Asn Lys Pro Ile Gln Val Val Tyr Val Pro Ser His
225                 230                 235                 240

Leu Phe His Met Leu Phe Glu Leu Phe Lys Asn Ser Met Arg Ala Thr
                245                 250                 255

Val Glu Leu His Glu Asn Arg Lys Glu Gly Tyr Pro Ala Val Lys Thr
            260                 265                 270

Leu Val Thr Leu Gly Lys Glu Asp Leu Ser Ile Lys Ile Ser Asp Leu
        275                 280                 285

Gly Gly Gly Val Pro Leu Arg Lys Ile Asp Arg Leu Phe Asn Tyr Met
        290                 295                 300

Tyr Ser Thr Ala Pro Arg Pro Ser Leu Glu Pro Thr Arg Ala Ala Pro
305                 310                 315                 320

Leu Ala Gly Phe Gly Tyr Gly Leu Pro Ile Ser Arg Leu Tyr Ala Arg
                325                 330                 335

Tyr Phe Gln Gly Asp Leu Lys Leu Tyr Ser Met Glu Gly Val Gly Thr
            340                 345                 350

Asp Ala Val Ile Tyr Leu Lys Ala Leu Ser Ser Glu Ser Phe Glu Arg
        355                 360                 365

Leu Pro Val Phe Asn Lys Ser Ala Trp Arg His Tyr Lys Thr Thr Pro
        370                 375                 380

Glu Ala Asp Asp Trp Ser Asn Pro Ser Ser Glu Pro Arg Asp Ala Ser
385                 390                 395                 400

Lys Tyr Lys Ala Lys Gln Asp Lys Ile Lys Thr Asn Arg Thr Leu
                405                 410                 415

<210> SEQ ID NO 12
<211> LENGTH: 23
<212> TYPE: DNA
<213> ORGANISM: Artificial Sequence
<220> FEATURE:
<223> OTHER INFORMATION: Synthetic Target sequence for partial
      modification of PDK1 gene (219-241 of SEQ ID NO: 6)

<400> SEQUENCE: 12
caatgatgtc attccaacca tgg                                           23

<210> SEQ ID NO 13
<211> LENGTH: 82
<212> TYPE: PRT
<213> ORGANISM: Artificial Sequence
<220> FEATURE:
<223> OTHER INFORMATION: Synthetic Polypeptide (2-8mPDK1_M1)

<400> SEQUENCE: 13
```

```
Met Phe Leu Arg Gln Glu Leu Pro Val Arg Leu Ala Asn Ile Met Lys
 1               5                  10                  15

Glu Ile Ser Leu Leu Pro Asp Asn Leu Leu Arg Thr Pro Ser Val Gln
            20                  25                  30

Leu Val Gln Ser Trp Tyr Ile Gln Ser Leu Gln Glu Leu Leu Asp Phe
        35                  40                  45

Lys Asp Lys Ser Ala Glu Asp Ala Lys Thr Ile Tyr Glu Phe Thr Asp
    50                  55                  60

Thr Val Ile Arg Ile Arg Asn Arg His Asn Asp Val Ile Pro Thr Pro
 65                  70                  75                  80

Arg Val

<210> SEQ ID NO 14
<211> LENGTH: 82
<212> TYPE: PRT
<213> ORGANISM: Artificial Sequence
<220> FEATURE:
<223> OTHER INFORMATION: Synthetic Polypeptide (2-8mPDK1_M2)

<400> SEQUENCE: 14

Met Phe Leu Arg Gln Glu Leu Pro Val Arg Leu Ala Asn Ile Met Lys
 1               5                  10                  15

Glu Ile Ser Leu Leu Pro Asp Asn Leu Leu Arg Thr Pro Ser Val Gln
            20                  25                  30

Leu Val Gln Ser Trp Tyr Ile Gln Ser Leu Gln Glu Leu Leu Asp Phe
        35                  40                  45

Lys Asp Lys Ser Ala Glu Asp Ala Lys Thr Ile Tyr Glu Phe Thr Asp
    50                  55                  60

Thr Val Ile Arg Ile Arg Asn Arg His Asn Asp Val Ile Pro Trp Pro
 65                  70                  75                  80

Arg Val

<210> SEQ ID NO 15
<211> LENGTH: 23
<212> TYPE: DNA
<213> ORGANISM: Artificial Sequence
<220> FEATURE:
<223> OTHER INFORMATION: Synthetic Target sequence for partial
      modification of PDK2 gene (172-194 of SEQ ID NO: 8)

<400> SEQUENCE: 15
cctgtgcgcc tggccaacat cat                                           23

<210> SEQ ID NO 16
<211> LENGTH: 62
<212> TYPE: PRT
<213> ORGANISM: Artificial Sequence
<220> FEATURE:
<223> OTHER INFORMATION: Synthetic Polypeptide (2-8mPDK2_m1)

<400> SEQUENCE: 16

Met Arg Trp Ile Arg Ala Leu Leu Lys Asn Ala Ser Leu Ala Gly Ala
 1               5                  10                  15

Pro Lys Tyr Ile Glu His Phe Ser Lys Phe Ser Pro Ser Pro Leu Ser
            20                  25                  30

Met Lys Gln Phe Leu Asp Phe Gly Ser Ser Asn Ala Cys Glu Lys Thr
        35                  40                  45

Ser Phe Thr Phe Leu Arg Gln Glu Leu Pro Val Pro Thr Ser
    50                  55                  60
```

<210> SEQ ID NO 17
<211> LENGTH: 65
<212> TYPE: PRT
<213> ORGANISM: Artificial Sequence
<220> FEATURE:
<223> OTHER INFORMATION: Synthetic Polypeptide (2-8mPDK2_m2)

<400> SEQUENCE: 17

Met Arg Trp Ile Arg Ala Leu Leu Lys Asn Ala Ser Leu Ala Gly Ala
 1               5                  10                  15

Pro Lys Tyr Ile Glu His Phe Ser Lys Phe Ser Pro Ser Pro Leu Ser
            20                  25                  30

Met Lys Gln Phe Leu Asp Phe Gly Ser Ser Asn Ala Cys Glu Lys Thr
        35                  40                  45

Ser Phe Thr Phe Leu Arg Gln Glu Leu Pro Gly Gln His His Glu Arg
    50                  55                  60

Asp
 65

<210> SEQ ID NO 18
<211> LENGTH: 65
<212> TYPE: PRT
<213> ORGANISM: Artificial Sequence
<220> FEATURE:
<223> OTHER INFORMATION: Synthetic Polypeptide (2-33mPDK2)

<400> SEQUENCE: 18

Met Arg Trp Ile Arg Ala Leu Leu Lys Asn Ala Ser Leu Ala Gly Ala
 1               5                  10                  15

Pro Lys Tyr Ile Glu His Phe Ser Lys Phe Ser Pro Ser Pro Leu Ser
            20                  25                  30

Met Lys Gln Phe Leu Asp Phe Gly Ser Ser Asn Ala Cys Glu Lys Thr
        35                  40                  45

Ser Phe Thr Phe Leu Arg Gln Glu Leu Pro Val Pro Ala Trp Pro Thr
    50                  55                  60

Ser
 65

<210> SEQ ID NO 19
<211> LENGTH: 23
<212> TYPE: DNA
<213> ORGANISM: Artificial Sequence
<220> FEATURE:
<223> OTHER INFORMATION: Synthetic Target sequence for partial
      modification of PDK3 gene (38-60 of SEQ ID NO: 10)

<400> SEQUENCE: 19
ccaaacagat cgagcgctac tcc                                              23

<210> SEQ ID NO 20
<211> LENGTH: 38
<212> TYPE: PRT
<213> ORGANISM: Artificial Sequence
<220> FEATURE:
<223> OTHER INFORMATION: Synthetic Polypeptide (2-8mPDK3)

<400> SEQUENCE: 20

Met Arg Leu Phe Phe Arg Leu Leu Lys Gln Pro Val Pro Lys Gln Asp
 1               5                  10                  15

Arg Ala Leu Leu Pro Leu Leu Ser Val Ser Ala Leu Tyr Gln Thr Val
            20                  25                  30

Leu Gly Leu Arg Lys Arg
        35

<210> SEQ ID NO 21
<211> LENGTH: 2490
<212> TYPE: DNA
<213> ORGANISM: Artificial Sequence
<220> FEATURE:
<223> OTHER INFORMATION: Synthetic pRGEN_CHO-PDK1_U6_SG vector
<220> FEATURE:
<221> NAME/KEY: promoter
<222> LOCATION: (84)..(324)
<223> OTHER INFORMATION: U6 promoter
<220> FEATURE:
<221> NAME/KEY: misc_feature
<222> LOCATION: (331)..(436)
<223> OTHER INFORMATION: RGEN transcript

<400> SEQUENCE: 21

| | | | | | |
|---|---|---|---|---|---|
| gacgaagact | caattgtcga | ttagtgaacg | gatctcgacg | gtatcgatca | cgagactagc | 60 |
| ctcgagcggc | cgcccccttc | accgagggcc | tatttcccat | gattccttca | tatttgcata | 120 |
| tacgatacaa | ggctgttaga | gagataattg | gaattaattt | gactgtaaac | acaaagatat | 180 |
| tagtacaaaa | tacgtgacgt | agaaagtaat | aatttcttgg | gtagtttgca | gttttaaaat | 240 |
| tatgttttaa | aatggactat | catatgctta | ccgtaacttg | aaagtatttc | gatttcttgg | 300 |
| ctttatatat | cttgtggaaa | ggacgaaaca | ccggcaatga | tgtcattcca | accagtttta | 360 |
| gagctagaaa | tagcaagtta | aaataaggct | agtccgttat | caacttgaaa | aagtggcacc | 420 |
| gagtcggtgc | ttttttctag | attcgcgatg | tacgggccag | atatacgcgt | tgacattgat | 480 |
| tattgactag | ttgtcttcct | gcattaatga | atcggccaac | gcgcggggag | aggcggtttg | 540 |
| cgtattgggc | gctcttccgc | ttcctcgctc | actgactcgc | tgcgctcggt | cgttcggctg | 600 |
| cggcgagcgg | tatcagctca | ctcaaaggcg | gtaatacggt | tatccacaga | atcaggggat | 660 |
| aacgcaggaa | agaacatgtg | agcaaaaggc | cagcaaaagg | ccaggaaccg | taaaaaggcc | 720 |
| gcgttgctgg | cgtttttcca | taggctccgc | ccccctgacg | agcatcacaa | aaatcgacgc | 780 |
| tcaagtcaga | ggtggcgaaa | cccgacagga | ctataaagat | accaggcgtt | tccccctgga | 840 |
| agctccctcg | tgcgctctcc | tgttccgacc | ctgccgctta | ccggatacct | gtccgccttt | 900 |
| ctcccttcgg | gaagcgtggc | gctttctcaa | tgctcacgct | gtaggtatct | cagttcggtg | 960 |
| taggtcgttc | gctccaagct | gggctgtgtg | cacgaacccc | ccgttcagcc | cgaccgctgc | 1020 |
| gccttatccg | gtaactatcg | tcttgagtcc | aacccggtaa | gacacgactt | atcgccactg | 1080 |
| gcagcagcca | ctggtaacag | gattagcaga | gcgaggtatg | taggcggtgc | tacagagttc | 1140 |
| ttgaagtggt | ggcctaacta | cggctacact | agaaggacag | tatttggtat | ctgcgctctg | 1200 |
| ctgaagccag | ttaccttcgg | aaaaagagtt | ggtagctctt | gatccggcaa | acaaaccacc | 1260 |
| gctggtagcg | gtggtttttt | tgtttgcaag | cagcagatta | cgcgcagaaa | aaaaggatct | 1320 |
| caagaagatc | ctttgatctt | ttctacgggg | tctgacgctc | agtggaacga | aaactcacgt | 1380 |
| taagggattt | tggtcatgag | attatcaaaa | aggatcttca | cctagatcct | tttaaattaa | 1440 |
| aaatgaagtt | ttaaatcaat | ctaaagtata | tatgagtaaa | cttggtctga | cagttaccaa | 1500 |
| tgcttaatca | gtgaggcacc | tatctcagcg | atctgtctat | ttcgttcatc | catagttgcc | 1560 |
| tgactcccccg | tcgtgtagat | aactacgata | cgggagggct | taccatctgg | ccccagtgct | 1620 |
| gcaatgatac | cgcgagatcc | acgctcaccg | gctccagatt | tatcagcaat | aaaccagcca | 1680 |
| gccggaaggg | ccgagcgcag | aagtggtcct | gcaactttat | ccgcctccat | ccagtctatt | 1740 |

```
aattgttgcc gggaagctag agtaagtagt tcgccagtta atagtttgcg caacgttgtt    1800
gccattgcta caggcatcgt ggtgtcacgc tcgtcgtttg gtatggcttc attcagctcc    1860
ggttcccaac gatcaaggcg agttacatga tcccccatgt tgtgcaaaaa agcggttagc    1920
tccttcggtc ctccgatcgt tgtcagaagt aagttggccg cagtgttatc actcatggtt    1980
atggcagcac tgcataattc tcttactgtc atgccatccg taagatgctt ttctgtgact    2040
ggtgagtact caaccaagtc attctgagaa tagtgtatgc ggcgaccgag ttgctcttgc    2100
ccggcgtcaa tacgggataa taccgcgcca catagcagaa ctttaaaagt gctcatcatt    2160
ggaaaacgtt cttcggggcg aaaactctca aggatcttac cgctgttgag atccagttcg    2220
atgtaaccca ctcgtgcacc caactgatct tcagcatctt ttactttcac cagcgtttct    2280
gggtgagcaa aaacaggaag gcaaaatgcc gcaaaaaagg gaataagggc gacacggaaa    2340
tgttgaatac tcatactctt cctttttcaa tattattgaa gcatttatca gggttattgt    2400
ctcatgagcg gatacatatt tgaatgtatt tagaaaaata aacaataggg gttccgcgc    2460
acatttcccc gaaaagtgcc acctgacgtc                                    2490
```

<210> SEQ ID NO 22
<211> LENGTH: 2490
<212> TYPE: DNA
<213> ORGANISM: Artificial Sequence
<220> FEATURE:
<223> OTHER INFORMATION: Synthetic pRGEN_CHO-PDK2_U6_SG vector
<220> FEATURE:
<221> NAME/KEY: promoter
<222> LOCATION: (84)..(324)
<223> OTHER INFORMATION: Synthetic U6 promoter
<220> FEATURE:
<221> NAME/KEY: misc_feature
<222> LOCATION: (331)..(436)
<223> OTHER INFORMATION: Synthetic RGEN transcript

<400> SEQUENCE: 22

```
gacgaagact caattgtcga ttagtgaacg gatctcgacg gtatcgatca cgagactagc      60
ctcgagcggc cgccccctte accgagggcc tatttcccat gattccttca tatttgcata    120
tacgatacaa ggctgttaga gagataattg gaattaattt gactgtaaac acaaagatat    180
tagtacaaaa tacgtgacgt agaaagtaat aatttcttgg gtagtttgca gttttaaaat    240
tatgttttaa aatggactat catatgctta ccgtaacttg aaagtatttc gatttcttgg    300
ctttatatat cttgtggaaa ggacgaaaca ccggatgatg ttggccaggc gcacgtttta    360
gagctagaaa tagcaagtta aaataaggct agtccgttat caacttgaaa aagtggcacc    420
gagtcggtgc ttttttctag attcgcgatg tacgggccag atatacgcgt tgacattgat    480
tattgactag ttgtcttcct gcattaatga atcggccaac gcgcgggag aggcggtttg    540
cgtattgggc gctcttccgc ttcctcgctc actgactcgc tgcgctcggt cgttcggctg    600
cggcgagcgg tatcagctca ctcaaaggcg gtaatacggt tatccacaga atcaggggat    660
aacgcaggaa agaacatgtg agcaaaaggc cagcaaaagg ccaggaaccg taaaaaggcc    720
gcgttgctgg cgttttttcca taggctccgc cccctgacg agcatcacaa aaatcgacgc    780
tcaagtcaga ggtggcgaaa cccgacagga ctataaagat accaggcgtt ccccctgga    840
agctccctcg tgcgctctcc tgttccgacc ctgccgctta ccggatacct gtccgccttt    900
ctcccttcgg gaagcgtggc gctttctcaa tgctcacgct gtaggtatct cagttcggtg    960
taggtcgttc gctccaagct gggctgtgtg cacgaacccc ccgttcagcc cgaccgctgc   1020
gccttatccg gtaactatcg tcttgagtcc aacccggtaa gacacgactt atcgccactg   1080
```

```
gcagcagcca ctggtaacag gattagcaga gcgaggtatg taggcggtgc tacagagttc    1140
ttgaagtggt ggcctaacta cggctacact agaaggacag tatttggtat ctgcgctctg    1200
ctgaagccag ttaccttcgg aaaaagagtt ggtagctctt gatccggcaa acaaaccacc    1260
gctggtagcg gtggtttttt tgtttgcaag cagcagatta cgcgcagaaa aaaggatct     1320 caagaagatc ctttgatctt ttctacgggg tctgacgctc agtggaacga aaactcacgt    1380
taagggattt tggtcatgag attatcaaaa aggatcttca cctagatcct tttaaattaa    1440
aaatgaagtt ttaaatcaat ctaaagtata tatgagtaaa cttggtctga cagttaccaa    1500
tgcttaatca gtgaggcacc tatctcagcg atctgtctat ttcgttcatc catagttgcc    1560
tgactccccg tcgtgtagat aactacgata cgggagggct taccatctgg ccccagtgct    1620
gcaatgatac cgcgagatcc acgctcaccg gctccagatt tatcagcaat aaaccagcca    1680
gccggaaggg ccgagcgcag aagtggtcct gcaactttat ccgcctccat ccagtctatt    1740
aattgttgcc gggaagctag agtaagtagt tcgccagtta atagtttgcg caacgttgtt    1800
gccattgcta caggcatcgt ggtgtcacgc tcgtcgtttg gtatggcttc attcagctcc    1860
ggttcccaac gatcaaggcg agttacatga tcccccatgt tgtgcaaaaa agcggttagc    1920
tccttcggtc ctccgatcgt tgtcagaagt aagttggccg cagtgttatc actcatggtt    1980
atggcagcac tgcataattc tcttactgtc atgccatccg taagatgctt ttctgtgact    2040
ggtgagtact caaccaagtc attctgagaa tagtgtatgc ggcgaccgag ttgctcttgc    2100
ccggcgtcaa tacgggataa taccgcgcca catagcagaa ctttaaaagt gctcatcatt    2160
ggaaaacgtt cttcggggcg aaaactctca aggatcttac cgctgttgag atccagttcg    2220
atgtaaccca ctcgtgcacc caactgatct tcagcatctt ttactttcac cagcgtttct    2280
gggtgagcaa aaacaggaag gcaaaatgcc gcaaaaaagg aataagggc gacacggaaa     2340 tgttgaatac tcatactctt cctttttcaa tattattgaa gcatttatca gggttattgt    2400
ctcatgagcg gatacatatt tgaatgtatt tagaaaaata acaaataggg gttccgcgc     2460 acatttcccc gaaaagtgcc acctgacgtc                                      2490
```

<210> SEQ ID NO 23
<211> LENGTH: 2490
<212> TYPE: DNA
<213> ORGANISM: Artificial Sequence
<220> FEATURE:
<223> OTHER INFORMATION: Synthetic pRGEN_CHO-PDK3_U6_SG vector
<220> FEATURE:
<221> NAME/KEY: promoter
<222> LOCATION: (84)..(324)
<223> OTHER INFORMATION: U6 promoter
<220> FEATURE:
<221> NAME/KEY: misc_feature
<222> LOCATION: (331)..(436)
<223> OTHER INFORMATION: RGEN transcript

<400> SEQUENCE: 23

```
gacgaagact caattgtcga ttagtgaacg gatctcgacg gtatcgatca cgagactagc     60
ctcgagcggc cgccccctcc accgagggcc tatttcccat gattccttca tatttgcata    120
tacgatacaa ggctgttaga gagataattg gaattaattt gactgtaaac acaaagatat    180
tagtacaaaa tacgtgacgt agaaagtaat aatttcttgg gtagtttgca gttttaaaat    240
tatgttttaa aatggactat catatgctta ccgtaacttg aaagtatttc gatttcttgg    300
ctttatatat cttgtggaaa ggacgaaaca ccggggagta gcgctcgatc tgttgtttta    360
```

```
gagctagaaa tagcaagtta aaataaggct agtccgttat caacttgaaa aagtggcacc        420
gagtcggtgc ttttttctag attcgcgatg tacgggccag atatacgcgt tgacattgat        480
tattgactag ttgtcttcct gcattaatga atcggccaac gcgcggggag aggcggtttg        540
cgtattgggc gctcttccgc ttcctcgctc actgactcgc tgcgctcggt cgttcggctg        600
cggcgagcgg tatcagctca ctcaaaggcg gtaatacggt tatccacaga atcaggggat        660
aacgcaggaa agaacatgtg agcaaaaggc cagcaaaagg ccaggaaccg taaaaaggcc        720
gcgttgctgg cgtttttcca taggctccgc cccccctgacg agcatcacaa aaatcgacgc       780
tcaagtcaga ggtggcgaaa cccgacagga ctataaagat accaggcgtt ccccctggaa        840
agctccctcg tgcgctctcc tgttccgacc ctgccgctta ccggatacct gtccgccttt        900
ctcccttcgg gaagcgtggc gctttctcaa tgctcacgct gtaggtatct cagttcggtg        960
taggtcgttc gctccaagct gggctgtgtg cacgaacccc ccgttcagcc cgaccgctgc       1020
gccttatccg gtaactatcg tcttgagtcc aacccggtaa gacacgactt atcgccactg       1080
gcagcagcca ctggtaacag gattagcaga gcgaggtatg taggcggtgc tacagagttc       1140
ttgaagtggt ggcctaacta cggctacact agaaggacag tatttggtat ctgcgctctg       1200
ctgaagccag ttaccttcgg aaaaagagtt ggtagctctt gatccggcaa acaaaccacc       1260
gctggtagcg gtggtttttt tgtttgcaag cagcagatta cgcgcagaaa aaaggatct        1320 caagaagatc ctttgatctt ttctacgggg tctgacgctc agtggaacga aaactcacgt       1380
taagggattt tggtcatgag attatcaaaa aggatcttca cctagatcct tttaaattaa       1440
aaatgaagtt ttaaatcaat ctaaagtata tatgagtaaa cttggtctga cagttaccaa       1500
tgcttaatca gtgaggcacc tatctcagcg atctgtctat ttcgttcatc catagttgcc       1560
tgactccccg tcgtgtagat aactacgata cgggagggct taccatctgg ccccagtgct       1620
gcaatgatac cgcgagatcc acgctcaccg gctccagatt tatcagcaat aaaccagcca       1680
gccggaaggg ccgagcgcag aagtggtcct gcaactttat ccgcctccat ccagtctatt       1740
aattgttgcc gggaagctag agtaagtagt tcgccagtta atagtttgcg caacgttgtt       1800
gccattgcta caggcatcgt ggtgtcacgc tcgtcgtttg gtatggcttc attcagctcc       1860
ggttcccaac gatcaaggcg agttacatga tcccccatgt tgtgcaaaaa agcggttagc       1920
tccttcggtc ctccgatcgt tgtcagaagt aagttggccg cagtgttatc actcatggtt       1980
atggcagcac tgcataattc tcttactgtc atgccatccg taagatgctt ttctgtgact       2040
ggtgagtact caaccaagtc attctgagaa tagtgtatgc ggcgaccgag ttgctcttgc       2100
ccggcgtcaa tacgggataa taccgcgcca catagcagaa ctttaaaagt gctcatcatt       2160
ggaaaacgtt cttcggggcg aaaactctca aggatcttac cgctgttgag atccagttcg       2220
atgtaaccca ctcgtgcacc caactgatct tcagcatctt ttactttcac cagcgtttct       2280
gggtgagcaa aaacaggaag gcaaatgccg caaaaaagg gaataagggc gacacggaaa        2340
tgttgaatac tcatactctt ccttttcaa tattattgaa gcatttatca gggttattgt        2400
ctcatgagcg gatacatatt tgaatgtatt tagaaaaata acaaataggg gttccgcgc        2460 acatttcccc gaaaagtgcc acctgacgtc                                        2490
```

<210> SEQ ID NO 24
<211> LENGTH: 1073
<212> TYPE: DNA
<213> ORGANISM: Artificial Sequence
<220> FEATURE:
<223> OTHER INFORMATION: Synthetic 2-8mPDK1_M1 coding PDK 1 gene with partial deletion

<400> SEQUENCE: 24

```
atgtttcttc gacaagagtt gcctgttaga ttggcaaata taatgaaaga aataagcctt      60
cttccagaca atcttctcag gacgccatca gtacagttgg tacaaagttg gtatatacag     120
agtcttcagg agctgcttga ttttaaggac aaaagtgctg aagatgctaa aactatttat     180
gaattcacag acacagtgat aaggatcaga aaccggcaca atgatgtcat tccaaccccc     240
agggtgtgac cgaatacaag gagagcttcg gggtggatcc tgtcaccagc caaaatgtcc     300
agtactttt ggatcgattc tacatgagtc gcatttcaat tagaatgtta ctcaaccagc      360
actctttatt gtttggtgga aaaggaagcc catctcatcg aaaacacatt ggaagcataa     420
atccaaactg cgatgtagtc gaagtcatta agatggcta tgaaaatgct aggcggcttt      480
gtgatttgta ttatgttaac tctcctgaac tagaacttga agaactaaat gcgatttcac     540
caggacagac aatacaagtg gtttatgtac catcccatct ctatcacatg gtgtttgaac     600
tgttcaagaa tgcaatgagg gctaccatgg agcaccatgc tgacaaaggt gtctatcccc     660
cgattcaagt tcatgtcaca ctgggtgagg aggatttgac tgtgaagatg agtgaccggg     720
gaggtggtgt tccactgaga aagattgaca gactcttcaa ctacatgtac tcaactgcac     780
cccggcctcg ttttgagaca tcccgtgcag tgcccctggc tggttttggt tatggattgc     840
ccatatcacg cctctatgca cagtacttcc aggggggacct aaagctgtac tccttggagg     900
gctacgggac tgacgctgtt atctatatta aggctctgtc aacagaatcc atcgagagac     960
tcccccgtgta taataaagct gcctggaagc attacaaaac caaccatgaa gctgacgact    1020
ggtgtgtccc cagcagagag ccgaaagaca tgaccacatt ccgaagctct tag            1073
```

<210> SEQ ID NO 25
<211> LENGTH: 1073
<212> TYPE: DNA
<213> ORGANISM: Artificial Sequence
<220> FEATURE:
<223> OTHER INFORMATION: Synthetic 2-8mPDK1_M2 coding PDK 1 gene with partial deletion

<400> SEQUENCE: 25

```
atgtttcttc gacaagagtt gcctgttaga ttggcaaata taatgaaaga aataagcctt      60
cttccagaca atcttctcag gacgccatca gtacagttgg tacaaagttg gtatatacag     120
agtcttcagg agctgcttga ttttaaggac aaaagtgctg aagatgctaa aactatttat     180
gaattcacag acacagtgat aaggatcaga aaccggcaca atgatgtcat tccatggccc     240
agggtgtgac cgaatacaag gagagcttcg gggtggatcc tgtcaccagc caaaatgtcc     300
agtactttt ggatcgattc tacatgagtc gcatttcaat tagaatgtta ctcaaccagc      360
actctttatt gtttggtgga aaaggaagcc catctcatcg aaaacacatt ggaagcataa     420
atccaaactg cgatgtagtc gaagtcatta agatggcta tgaaaatgct aggcggcttt      480
gtgatttgta ttatgttaac tctcctgaac tagaacttga agaactaaat gcgatttcac     540
caggacagac aatacaagtg gtttatgtac catcccatct ctatcacatg gtgtttgaac     600
tgttcaagaa tgcaatgagg gctaccatgg agcaccatgc tgacaaaggt gtctatcccc     660
cgattcaagt tcatgtcaca ctgggtgagg aggatttgac tgtgaagatg agtgaccggg     720
gaggtggtgt tccactgaga aagattgaca gactcttcaa ctacatgtac tcaactgcac     780
cccggcctcg ttttgagaca tcccgtgcag tgcccctggc tggttttggt tatggattgc     840
```

```
ccatatcacg cctctatgca cagtacttcc aggggggacct aaagctgtac tccttggagg      900
gctacgggac tgacgctgtt atctatatta aggctctgtc aacagaatcc atcgagagac      960
tccccgtgta ataaaagct gcctggaagc attacaaaac caaccatgaa gctgacgact     1020
ggtgtgtccc cagcagagag ccgaaagaca tgaccacatt ccgaagctct tag            1073
```

<210> SEQ ID NO 26
<211> LENGTH: 1217
<212> TYPE: DNA
<213> ORGANISM: Artificial Sequence
<220> FEATURE:
<223> OTHER INFORMATION: Synthetic 2-8mPDK2_m1 coding PDK 2 gene with
      partial deletion

<400> SEQUENCE: 26

```
atgcgctgga tccgggcact gttgaagaat gcgtccctag cagggggcgcc caagtacatc     60 gagcacttca gcaagttctc cccgtccccg ctgtccatga agcagtttct agacttcgga    120
tccagcaatg cctgcgagaa aacttccttc accttcctta ggcaggagct gcctgtgcca    180
acatcatgaa agagattaac ttgcttcccg acagagtgct gggcaccccc tcagtgcagc    240
tggtgcagag ctggtatgtc cagagtctgc tggacatcat ggaattcctg acaaggatc     300 cagaggatca ccggacacta agccagttca ccgatgccct ggtcaccatc cggaaccggc    360
acaatgacgt agtgcccacc atggcacagg gagtgctgga gtacaaggac acctatggcg    420
atgacccggt gtccaaccag aacattcagt acttcttgga ccgcttctac ctcagccgga    480
tctccatccg catgctcatc aaccagcaca ccctcatctt tgatggaagt accaacccag    540
ctcaccccaa acacattggc agcattgacc ctaactgcag cgtgtctgat gtggtaaaag    600
atgcctatga catggccaag ctcctgtgtg acaaatacta catggcttca cctgatctag    660
agatccagga agttaatgcc accaatgcca accagcccat tcacatggtc tacgtcccct    720
cccacctcta ccacatgctc tttgagctct tcaagaatgc catgcgggcc acggtggaga    780
gccacgagtc cagcctcacc ctccctccta tcaagattat ggtagccttg ggtgaagaag    840
atctgtccat caaaatgagt gaccgaggtg gggtgtccc cttgaggaag attgagaggc    900
tcttcagcta catgtactcc acagccccca cccccagcc tggcactggg ggtaccccac    960
tggctggctt tgggtatgga ctccccattt cccgcctcta cgccaagtac ttccaaggag   1020
acttgcagct cttctctatg gagggctttg gacagatgc tgtcatatat ctcaaggccc   1080
tgtccacgga ctcagtggag cgtctgcctg tctacaacaa gtctgcctgg cgccactacc   1140
agaccatcca ggaggccggt gactggtgtg tgcccagcac ggagcccaag aacacatcca   1200
cgtatcgggt cagctag                                                  1217
```

<210> SEQ ID NO 27
<211> LENGTH: 1216
<212> TYPE: DNA
<213> ORGANISM: Artificial Sequence
<220> FEATURE:
<223> OTHER INFORMATION: Synthetic 2-8mPDK2_m2 coding PDK 2 gene with
      partial deletion

<400> SEQUENCE: 27

```
atgcgctgga tccgggcact gttgaagaat gcgtccctag cagggggcgcc caagtacatc     60 gagcacttca gcaagttctc cccgtccccg ctgtccatga agcagtttct agacttcgga    120
tccagcaatg cctgcgagaa aacttccttc accttcctta ggcaggagct gcctggccaa    180
catcatgaaa gagattaact tgcttcccga cagagtgctg gcaccccct cagtgcagct     240
```

```
ggtgcagagc tggtatgtcc agagtctgct ggacatcatg gaattcctgg acaaggatcc    300
agaggatcac cggacactaa gccagttcac cgatgccctg gtcaccatcc ggaaccggca    360
caatgacgta gtgcccacca tggcacaggg agtgctggag tacaaggaca cctatggcga    420
tgacccggtg tccaaccaga acattcagta cttcttggac cgcttctacc tcagccggat    480
ctccatccgc atgctcatca accagcacac cctcatcttt gatggaagta ccaacccagc    540
tcaccccaaa cacattggca gcattgaccc taactgcagc gtgtctgatg tggtaaaaga    600
tgcctatgac atggccaagc tcctgtgtga caaatactac atggcttcac ctgatctaga    660
gatccaggaa gttaatgcca ccaatgccaa ccagcccatt cacatggtct acgtcccctc    720
ccacctctac cacatgctct ttgagctctt caagaatgcc atgcgggcca cggtggagag    780
ccacgagtcc agcctcaccc tccctcctat caagattatg gtagccttgg gtgaagaaga    840
tctgtccatc aaaatgagtg accgaggtgg gggtgtcccc ttgaggaaga ttgagaggct    900
cttcagctac atgtactcca gcccccac  accccagcct ggcactgggg gtaccccact    960
ggctggcttt gggtatggac tccccatttc ccgcctctac gccaagtact ccaaggaga    1020 cttgcagctc ttctctatgg agggctttgg gacagatgct gtcatatatc tcaaggccct    1080
gtccacggac tcagtggagc gtctgcctgt ctacaacaag tctgcctggc ccactacca    1140 gaccatccag gaggccggtg actggtgtgt gcccagcacg gagcccaaga acacatccac    1200
gtatcgggtc agctag                                                    1216

<210> SEQ ID NO 28
<211> LENGTH: 1226
<212> TYPE: DNA
<213> ORGANISM: Artificial Sequence
<220> FEATURE:
<223> OTHER INFORMATION: Synthetic 2-33mPDK2 coding PDK 2 gene with
      partial insertion

<400> SEQUENCE: 28
atgcgctgga tccgggcact gttgaagaat gcgtccctag caggggcgcc caagtacatc     60
gagcacttca gcaagttctc cccgtccccg ctgtccatga gcagtttct agacttcgga    120 tccagcaatg cctgcgagaa aacttccttc accttcctta ggcaggagct gcctgtgccc    180
gcctggccaa catcatgaaa gagattaact tgcttcccga cagagtgctg ggcacccct    240 cagtgcagct ggtgcagagc tggtatgtcc agagtctgct ggacatcatg gaattcctgg    300
acaaggatcc agaggatcac cggacactaa gccagttcac cgatgccctg gtcaccatcc    360
ggaaccggca caatgacgta gtgcccacca tggcacaggg agtgctggag tacaaggaca    420
cctatggcga tgacccggtg tccaaccaga acattcagta cttcttggac cgcttctacc    480
tcagccggat ctccatccgc atgctcatca accagcacac cctcatcttt gatggaagta    540
ccaacccagc tcaccccaaa cacattggca gcattgaccc taactgcagc gtgtctgatg    600
tggtaaaaga tgcctatgac atggccaagc tcctgtgtga caaatactac atggcttcac    660
ctgatctaga gatccaggaa gttaatgcca ccaatgccaa ccagcccatt cacatggtct    720
acgtcccctc ccacctctac cacatgctct ttgagctctt caagaatgcc atgcgggcca    780
cggtggagag ccacgagtcc agcctcaccc tccctcctat caagattatg gtagccttgg    840
gtgaagaaga tctgtccatc aaaatgagtg accgaggtgg gggtgtcccc ttgaggaaga    900
ttgagaggct cttcagctac atgtactcca gcccccacac accccagcct ggcactgggg    960
gtaccccact ggctggcttt gggtatggac tccccatttc ccgcctctac gccaagtact   1020
```

```
tccaaggaga cttgcagctc ttctctatgg agggctttgg gacagatgct gtcatatatc    1080
tcaaggccct gtccacggac tcagtggagc gtctgcctgt ctacaacaag tctgcctggc    1140
gccactacca gaccatccag gaggccggtg actggtgtgt gcccagcacg gagcccaaga    1200
acacatccac gtatcgggtc agctag                                         1226
```

<210> SEQ ID NO 29
<211> LENGTH: 1249
<212> TYPE: DNA
<213> ORGANISM: Artificial Sequence
<220> FEATURE:
<223> OTHER INFORMATION: Synthetic 2-8mPDK3 coding PDK 3 gene with partial insertion

<400> SEQUENCE: 29

```
atgcggctct tctttaggct gctcaagcag ccggtgccca acaagatcg agcgctactc      60 ccgcttctct ccgtctccgc tctctatcaa acagttcttg gacttcggaa gagataatgc    120
atgtgaaaaa acttcatata tgtttctgcg caaggagctt cctgtacgac tggcgaacac    180
aatgagagaa gttaatcttt tgccggataa cttgttgaac cgcccttcag tgggattagt    240
tcagagttgg tacatgcaga gctttcttga acttttagaa tatgaaaaca agagcccaga    300
agacccacgg gttttagata actttctcca tgttttgatt aatatcagaa acagacacaa    360
cgatgttgtt cccacaatgg cccaaggcgt gattgagtac aaagaaaagt tcggatttga    420
tccatttatt agcagtaaca tccagtattt cctggatcgt ttttatacca accgcatctc    480
tttccgaatg cttattaacc aacacacact tctgtttggt ggtgacacta atcctgctca    540
tcctaagcac atagggagta tcgatcccac ctgtaatgta gctgatgtcg tgaaagatgc    600
atatgaaaca gctaagctac tctgtgaaca gtattacctg gtagctccag agctggaagt    660
ggaagaattc aatgccaaag caccaaacaa acctattcag gtggtttatg tgccgtctca    720
tctgtttcac atgctatttg agctgttcaa gaactcgatg agagcaacag ttgaactaca    780
tgaaaataga aagagggct acccagctgt taaaactctc gttactcttg gtaaagaaga    840
cttgtccatt aagataagtg acttaggtgg tggagtccca cttcgaaaaa tagaccgtct    900
ttttaactac atgtattcca ctgctcctcg acccagcctg gagcctacaa gagctgctcc    960
cttggctgga tttggttatg gcttgccaat ttctcgactg tatgccagat attttcaggg    1020
agatctaaaa ctgtattcca tggaaggagt gggtaccgat gctgttattt atctgaaggc    1080
cctttcaagt gaatcatttg agaggctgcc cgttttcaat aagtctgcat ggcgccatta    1140
caagacaact cctgaagctg atgactggag caatcccagt agcgaaccaa gggatgcatc    1200
aaaatacaag gctaaacagg acaagatcaa gactaataga actttgtag              1249
```

<210> SEQ ID NO 30
<211> LENGTH: 21
<212> TYPE: DNA
<213> ORGANISM: Artificial Sequence
<220> FEATURE:
<223> OTHER INFORMATION: Synthetic PDK1 Forward primer

<400> SEQUENCE: 30

```
gggaaaccct taacactgct c                                               21
```

<210> SEQ ID NO 31
<211> LENGTH: 20
<212> TYPE: DNA
<213> ORGANISM: Artificial Sequence

```
<220> FEATURE:
<223> OTHER INFORMATION: Synthetic PDk1 reverse primer

<400> SEQUENCE: 31
atcaaaagcg aaaagccaaa                                               20

<210> SEQ ID NO 32
<211> LENGTH: 21
<212> TYPE: DNA
<213> ORGANISM: Artificial Sequence
<220> FEATURE:
<223> OTHER INFORMATION: Synthetic PDK2 forward primer

<400> SEQUENCE: 32
ttgaggtgac ttaggccaga a                                             21

<210> SEQ ID NO 33
<211> LENGTH: 20
<212> TYPE: DNA
<213> ORGANISM: Artificial Sequence
<220> FEATURE:
<223> OTHER INFORMATION: Synthetic PDK2 reverse primer

<400> SEQUENCE: 33
gccaagggtt actgctgaca                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic PDK3 forward primer

<400> SEQUENCE: 34
actgcctctg gtgcttgttt                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic PDK3 reverse primer

<400> SEQUENCE: 35
tgagagtcct tggaggaagc                                               20
```

METHOD FOR PRODUCING POLYPEPTIDES USING PDK-INACTIVATED CELLS

CROSS-REFERENCE TO RELATED APPLICATIONS

This application claims the benefit of Korean Patent Application No. 10-2014-0150701 filed on Oct. 31, 2014 in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 64,923 Byte ASCII (Text) file named "722174_ST25 TXT-Revised" created on Jan. 13, 2016.

BACKGROUND OF THE INVENTION

1. Field

Provided is a recombinant cell including inactivated pyruvate dehydrogenase kinase (PDK) gene, a composition for producing a polypeptide of interest including the recombinant cell, and a method of producing a polypeptide of interest using the recombinant cell.

2. Description of the Related Art

More efficient processes for economical production of therapeutic proteins, such as antibodies, are needed.

In case of antibodies, all approved antibody products have been produced using a mammalian cell as a host cell. The mammalian cell has some advantages in that the safety is proven and glycosylation which is important for antibody activities normally occurs. Due to such advantages, the mammalian cell has been regarded as the most proper expression system for antibody production. However, the mammalian cell has some disadvantages, such as slow growth rate and low productivity.

BRIEF SUMMARY OF THE INVENTION

An embodiment provides a recombinant vector for inactivation of pyruvate dehydrogenase kinase (PDK) gene.

Another embodiment provides a recombinant cell including an inactivated PDK gene.

Another embodiment provides a recombinant cell including an inactivated PDK gene and a recombinant vector encoding a polypeptide of interest. The recombinant cell may be useful as a cell for production of the polypeptide of interest.

Another embodiment provides a composition for production of a polypeptide of interest including the recombinant vector or the recombinant cell.

Another embodiment provides a method of production of a polypeptide of interest using the recombinant vector or the recombinant cell.

Still another embodiment provides a method of increasing production of a polypeptide of interest in a cell by inactivating a PDK gene in the cell, such as a mammalian cell.

BRIEF DESCRIPTION OF THE DRAWINGS

FIG. 6 shows genetic information of a clone having a partial deletion of PDK1 gene.

FIG. 7 shows genetic information of a clone having a partial deletion of PDK2 gene.

DETAILED DESCRIPTION OF THE INVENTION

Figure 1:
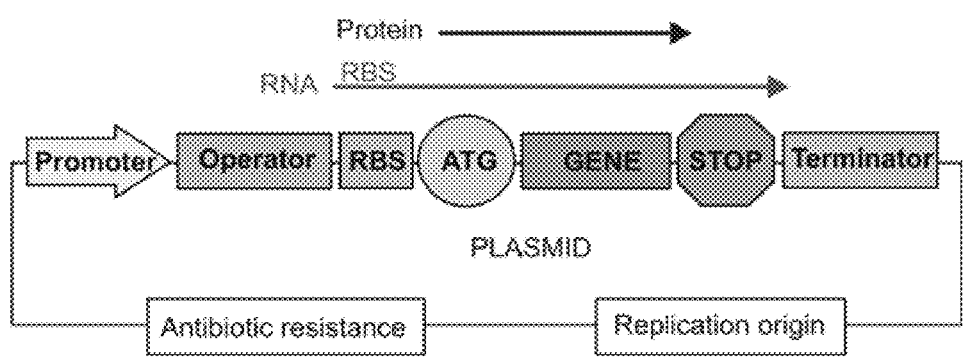
FIG. 1 is a schematic view illustrating a general structure of a recombinant vector.

An embodiment provides a recombinant vector for inactivation of pyruvate dehydrogenase kinase (PDK) gene.

Another embodiment provides a recombinant cell including inactivated PDK gene. The recombinant cell is GSKO-PDK2-8 deposited with Accession No. KCLRF-BP-00328.

Another embodiment provides a recombinant cell including inactivated PDK gene and a gene encoding a polypeptide of interest. The recombinant cell may be useful as a cell for production of the polypeptide of interest.

Another embodiment provides a composition for production of a polypeptide of interest including the recombinant vector or the recombinant cell.

Another embodiment provides a method of production of a polypeptide of interest using the recombinant vector or the recombinant cell.

Still another embodiment provides a method of increasing production of a polypeptide of interest, including inactivating PDK gene in a cell, such as a mammalian cell.

Pyruvate dehydrogenase kinase (PDK; EC 2.7.11.2) phosphorylates and inactivates pyruvate dehydrogenase. The term "PDK" may cover PDK1, PDK2, PDK3, and PDK4. In this disclosure, PDK protein or PDK gene may be at least one selected from the group consisting of PDK1, PDK2, PDK3, and PDK4 proteins or at least one selected from the group consisting of PDK1, PDK2, PDK3, and PDK4 genes, respectively. For example, PDK protein or gene may be from any prokaryote (such as, *Escherichia coli*, etc.) or any mammal or any mammalian cell, such as from a primate (e.g., human, monkey, etc.), a rodents (e.g., hamster, rat, mouse, etc.), and the like.

In one embodiment, the PDK protein or gene may be from a CHO (Chinese hamster ovary) cell, for example, at least one selected from the group consisting of CHO PDK1 (NCBI Accession No. EGV95676.1), CHO PDK2 (NCBI Accession No. EGW01786.1), CHO PDK3 (NCBI Accession No. EGV96253.1), and CHO PDK4 (NCBI Accession No. EGW06951.1, EGW06952.1) proteins, or genes encoding the proteins, but not be limited thereto. For example, the PDK protein or gene may be from a mammalian cell as described below or an endogenous protein or gene therein.

The "inactivation of PDK gene" refers to disruption of the PDK gene, such as by mutation or treatment with an expression inhibitor. Inactivation of the PDK gene may be accomplished by deletion or substitution of the entire PDK gene, deletion or substitution of a part of PDK gene, insertion of at least one nucleotide into the PDK gene, and/or treatment of a PDK gene with an expression inhibitor. The PDK gene may be endogenous in a genome of a host cell. The term "inactivated PDK gene" may also refer to a PDK gene that cannot be expressed or cannot encode a PDK protein having normal functions, such as by deletion or substitution of an entire PDK gene, deletion or substitution of a part of a PDK gene, insertion of at least one nucleotide into a PDK gene, and/or treatment with a PDK gene expression inhibitor.

As used herein, the PDK gene may refer to DNA, cDNA, or mRNA encoding a PDK protein, and may be an endogenous gene in a host cell.

The deletion of an entire PDK gene may refer to a complete deletion of whole PDK gene from a chromosome or genome.

The deletion or substitution of a part of a PDK gene may refer to a deletion or substitution of part of a coding region, part of a non-coding region, and/or part of an expression (transcription) regulatory region (e.g., promoter, etc.) of a PDK gene. When all or part of a PDK gene is substituted, such substitution may be with any nucleotide or nucleotide sequence that is different from the original nucleotide or nucleotide sequence present in a wild-type PDK gene, thereby creating a PDK gene that does not express a PDK protein or expresses a PDK protein with abnormal functions due, for example, to a change in the open reading frame. For example, the deletion or substitution of all or part of a PDK gene may comprise deletion or substitution in a coding region, non-coding region, or expression (transcription) regulatory region of a PDK gene, at least one nucleotide, for example, about 1 to about 1000 nucleotides, about 1 to about 500 nucleotides, about 1 to about 300 nucleotides, about 1 to about 200 nucleotides, about 1 to about 100 nucleotides, about 1 to about 50 nucleotides, about 1 to about 30 nucleotides, about 1 to about 20 nucleotides, about 1 to about 10 nucleotides, about 1 to about 7 nucleotides, about 1 to about 5 nucleotides, about 2 to about 1000 nucleotides, about 2 to about 500 nucleotides, about 2 to about 300 nucleotides, about 2 to about 200 nucleotides, about 2 to about 100 nucleotides, about 2 to about 50 nucleotides, about 2 to about 30 nucleotides, about 2 to about 20 nucleotides, about 2 to about 10 nucleotides, about 2 to about 7 nucleotides, about 2 to about 5 nucleotides, about 5 to about 1000 nucleotides, about 5 to about 500 nucleotides, about 5 to about 300 nucleotides, about 5 to about 200 nucleotides, about 5 to about 100 nucleotides, about 5 to about 50 nucleotides, about 5 to about 30 nucleotides, about 5 to about 20 nucleotides, about 5 to about 10 nucleotides, about 10 to about 1000 nucleotides, about 10 to about 500 nucleotides, about 10 to about 300 nucleotides, about 10 to about 200 nucleotides, about 10 to about 100 nucleotides, about 10 to about 50 nucleotides, about 10 to about 30 nucleotides, or about 10 to about 20 nucleotides. When substituted, the substitution may be with a nucleotide or nucleotide sequence that is different from the original nucleotide in the wild-type PDK gene, including substitution with a modified nucleotide (e.g., by methylation, etc.). In an embodiment, the deletion or substitution may be conducted at coding region, cDNA, mRNA, non-coding region, and/or expression regulatory region (e.g., promoter, etc.) of a PDK gene.

The term "at least one nucleotide insertion" may refer to addition of at least one nucleotide into a site of PDK gene, leading to non-expression of a PDK protein or expression of a PDK protein with abnormal functions (e.g., an inactive or partially active PDK protein). For example, the "at least one nucleotide insertion" may refer to addition of at least one nucleotide, for example, about 1 to about 1000 nucleotides, about 1 to about 500 nucleotides, about 1 to about 300 nucleotides, about 1 to about 200 nucleotides, about 1 to about 100 nucleotides, about 1 to about 50 nucleotides, about 1 to about 30 nucleotides, about 1 to about 20 nucleotides, about 1 to about 10 nucleotides, about 1 to about 7 nucleotides, about 1 to about 5 nucleotides, about 1 to about 3 nucleotides, about 2 to about 1000 nucleotides, about 2 to about 500 nucleotides, about 2 to about 300 nucleotides, about 2 to about 200 nucleotides, about 2 to about 100 nucleotides, about 2 to about 50 nucleotides, about 2 to about 30 nucleotides, about 2 to about 20 nucleotides, about 2 to about 10 nucleotides, about 2 to about 7 nucleotides, about 2 to about 5 nucleotides, about 2 to about 3 nucleotides, about 5 to about 1000 nucleotides, about 5 to about 500 nucleotides, about 5 to about 300 nucleotides, about 5 to about 200 nucleotides, about 5 to about 100 nucleotides, about 5 to about 50 nucleotides, about 5 to about 30 nucleotides, about 5 to about 20 nucleotides, about 5 to about 10 nucleotides, about 10 to about 1000 nucleotides, about 10 to about 500 nucleotides, about 10 to about 300 nucleotides, about 10 to about 200 nucleotides, about 10 to about 100 nucleotides, about 10 to about 50 nucleotides, about 10 to about 30 nucleotides, or about 10 to about 20 nucleotides, to a site positioned within PDK gene. The nucleotide to be added may be at least one selected from A, T (or U), G, C, and modified nucleotides (e.g., a methylated nucleotide, etc.). In an embodiment, the site of PDK gene where the nucleotide insertion (addition) occurs may be positioned in a coding region, cDNA, mRNA, non-coding region, and/or expression regulatory region (e.g., promoter, etc.) of a PDK gene.

The PDK gene expression inhibitor may be at least one selected from the group consisting of chemicals (e.g., small molecular compounds or pharmaceutically acceptable salts thereof), proteins (e.g., antibodies or antigen-binding fragments thereof), single-stranded or double-stranded nucleic acid molecules (e.g., aptamers, antisense oligonucleotides, siRNAs (small interfering RNAs), shRNAs (small hairpin RNAs), miRNA (microRNAs), etc.) and the like, which specifically recognize and/or bind to a PDK gene and/or otherwise inhibit expression or function thereof. For example, the PDK gene expression inhibitor may be at least one selected from single-stranded or double-stranded nucleic acid molecules (e.g., aptamers, antisense oligonucleotides, siRNAs (small interfering RNAs), shRNAs (small hairpin RNAs), miRNA (microRNAs), etc.), which specifically bind to (or have complementary sequence to or hybridize with) all or part (e.g., about 5 to about 100 bp, about 5 to about 50 bp, about 5 to about 30 bp, or about 5 to about 25 bp) of a PDK gene.

The partial deletion or substitution of PDK gene or the nucleotide insertion into PDK gene may be conducted within a certain region (hereinafter, "a target region") of PDK gene. The target region may be a consecutive nucleotide sequence region of about 5 to about 100 bp, for example, about 5 to about 50 bp, about 10 to about 50 bp, about 20 to about 50 bp, about 5 to about 40 bp, about 10 to about 40 bp, about 20 to about 40 bp, about 5 to about 30 bp, about 10 to about 30 bp, or about 20 to about 30 bp, within a PDK gene (e.g., SEQ ID NO: 6, SEQ ID NO: 8 or SEQ ID NO: 10), which comprises a site where the partial deletion or substitution of PDK gene or the insertion of a nucleotide into PDK gene occurs.

The partial deletion or substitution of PDK gene may be a deletion or substitution wherein at least one nucleotide (e.g., about 1 to about 50 nucleotides, about 1 to about 40 nucleotides, about 1 to about 30 nucleotides, about 1 to about 20 nucleotides, or about 1 to about 10 nucleotides) in a consecutive nucleotide sequence region of about 5 to about 100 bp (e.g., about 5 to about 50 bp, about 10 to about 50 bp, about 20 to about 50 bp, about 5 to about 40 bp, about 10 to about 40 bp, about 20 to about 40 bp, about 5 to about 30 bp, about 10 to about 30 bp, or about 20 to about 30 bp) within PDK gene (e.g., SEQ ID NO: 6, SEQ ID NO: 8, or SEQ ID NO: 10), is deleted, or is substituted with a nucleotide different from that of wild-type PDK gene.

In case of a partial deletion or substitution of PDK1 gene or a nucleotide insertion into PDK1 gene, the target region may be a consecutive nucleotide sequence region of about 23 to about 100 bp, about 23 to about 50 bp, about 23 to about 40 bp, or about 23 to about 30 bp, comprising the consecutive sequence from $235^{th}$ position to $241^{st}$ position of PDK1 gene (e.g., SEQ ID NO: 6). For example, the target region of PDK1 gene may comprise or consisting essentially of SEQ ID NO: 12, which is the sequence from $219^{th}$ position to $241^{st}$ position of SEQ ID NO: 6. The partial deletion or substitution of PDK1 gene or a nucleotide insertion into PDK1 gene may refer to a deletion, substitution, or insertion wherein at least one nucleotide (e.g., about 1 to about 20 nucleotides, about 1 to about 15 nucleotides, about 1 to about 10 nucleotides, about 1 to about 7 nucleotides, about 1 to about 5 nucleotides, about 2 to about 20 nucleotides, about 2 to about 15 nucleotides, about 2 to about 10 nucleotides, about 2 to about 7 nucleotides, or about 2 to about 5 nucleotides) selected from a target region (i.e., a consecutive nucleotide sequence region of about 23 to about 100 bp, about 23 to about 50 bp, about 23 to about 40 bp, or about 23 to about 30 bp, which comprises the consecutive sequence from $235^{th}$ position to $241^{st}$ position of SEQ ID NO: 6), for example, selected from SEQ ID NO: 12, is deleted or substituted with a nucleotide different from that of wild-type PDK1 gene, or a certain nucleotide is inserted into upstream or downstream of the selected at least one nucleotide. For example, the partial deletion or substitution of PDK1 gene or a nucleotide insertion into PDK1 gene may be one in which 1 to 7 nucleotides from the $235^{th}$ to $241^{st}$ positions of SEQ ID NO: 6 are deleted or substituted with a different nucleotide or nucleotide sequence. In an embodiment, the partial deletion or substitution of PDK1 gene or a nucleotide insertion into PDK1 gene may be a deletion of the sequence (atgg) from $238^{th}$ position to $241^{st}$ position of SEQ ID NO: 6, or a deletion of the sequence (acca) from $235^{th}$ position to $238^{th}$ position of SEQ ID NO: 6; but not be limited thereto.

In case of a partial deletion or substitution of PDK2 gene or a nucleotide insertion into PDK2 gene, the target region may be a consecutive nucleotide sequence region of about 23 to about 100 bp, about 23 to about 50 bp, about 23 to about 40 bp, or about 23 to about 30 bp, comprising the consecutive sequence from $172^{nd}$ position to $194^{th}$ position of PDK2 gene (e.g., SEQ ID NO: 8). For example, the target region of PDK2 gene may comprise or consisting essentially of SEQ ID NO: 15, which is the sequence from $172^{nd}$ position to $194^{th}$ position of SEQ ID NO: 8. The partial deletion or substitution of PDK2 gene or a nucleotide insertion into PDK2 gene may refer to a deletion, substitution, or insertion wherein at least one nucleotide (e.g., about 1 to about 20 nucleotides, about 1 to about 15 nucleotides, about 1 to about 10 nucleotides, about 1 to about 7 nucleotides, about 1 to about 5 nucleotides, about 2 to about 20 nucleotides, about 2 to about 15 nucleotides, about 2 to about 10 nucleotides, about 2 to about 7 nucleotides, or about 2 to about 5 nucleotides) selected from a target region (i.e., a consecutive nucleotide sequence region of about 23 to about 100 bp, about 23 to about 50 bp, about 23 to about 40 bp, or about 23 to about 30 bp, which comprises the consecutive sequence from $172^{nd}$ position to $194^{th}$ position of SEQ ID NO: 8), for example, selected from SEQ ID NO: 15, is deleted or substituted with a nucleotide different from that of wild-type PDK2 gene, or a certain nucleotide is inserted into upstream or downstream of the selected at least one nucleotide. For example, the partial deletion or substitution of PDK2 gene or a nucleotide insertion into PDK2 gene may be one in which 1 to 20 nucleotides from the $172^{nd}$ to $194^{th}$ positions of SEQ ID NO: 8 are deleted or substituted with a different nucleotide or nucleotide sequence, and/or 1 to 20 nucleotides are inserted within the region from the $172^{nd}$ to $194^{th}$ positions of SEQ ID NO: 8. In an embodiment, the partial deletion or substitution of PDK2 gene or a nucleotide insertion into PDK2 gene may be a deletion of the sequence (gcgcctg) from $177^{th}$ position to $183^{rd}$ position of SEQ ID NO: 8, a deletion of the sequence (tgcgcctg) from $176^{th}$ position to $183^{rd}$ position of SEQ ID NO: 8, or an insertion of at least one nucleotide (e.g., about 1 to about 5 nucleotides or about 1 to about 3 nucleotides) at the $180^{th}$ position of SEQ ID NO: 8 (i.e., between the 3'-end of the $179^{th}$ nucleotide and the 5'-end of the $180^{th}$ nucleotide of SEQ ID NO: 8), wherein each of the at least one nucleotide to be inserted may be independently selected from A, T (or U), G, C, and modified nucleotides (e.g., methylated nucleotide, etc.); but not be limited thereto.

In case of a partial deletion or substitution of PDK3 gene or a nucleotide insertion into PDK3 gene, the target region may be a consecutive nucleotide sequence region of about 23 to about 100 bp, about 23 to about 50 bp, about 23 to about 40 bp, or about 23 to about 30 bp, comprising the consecutive sequence from $38^{th}$ position to $60^{th}$ position of PDK3 gene (e.g., SEQ ID NO: 10). For example, the target region of PDK3 gene may comprise or consisting essentially of SEQ ID NO: 19, which is the sequence from $38^{th}$ position to $60^{th}$ position of SEQ ID NO: 10. The partial deletion or substitution of PDK2 gene or a nucleotide insertion into PDK2 gene may refer to a deletion, substitution, or insertion wherein at least one nucleotide (e.g., about 1 to about 20 nucleotides, about 1 to about 15 nucleotides, about 1 to about 10 nucleotides, about 1 to about 7 nucleotides, about 1 to about 5 nucleotides, or about 1 to about 3 nucleotides) selected from a target region (i.e., a consecutive nucleotide sequence region of about 23 to about 100 bp, about 23 to about 50 bp, about 23 to about 40 bp, or about 23 to about 30 bp, which comprises the consecutive sequence from $38^{th}$ position to $60^{th}$ position of SEQ ID NO: 10), for example, selected from SEQ ID NO: 19, is deleted or substituted with a nucleotide different from that of wild-type PDK3 gene, or a certain nucleotide is inserted into upstream or downstream of the selected at least one nucleotide. For example, the partial deletion or substitution of PDK2 gene or nucleotide insertion into PDK2 gene may be one in which 1 to 20 nucleotides are inserted within the region from the $38^{th}$ to $60^{th}$ positions of SEQ ID NO: 10. In an embodiment, the partial deletion or substitution of PDK3 gene or a nucleotide insertion into PDK3 gene may be an insertion of a nucleotide at the 45$^{th}$ position of SEQ ID NO: 10 (i.e., between the 3'-end of the 44$^{th}$ nucleotide and the 5'-end of the 45$^{th}$ nucleotide of SEQ ID NO: 10), wherein the nucleotide to be inserted may be selected from A, T (or U), G, C, and modified nucleotides (e.g., methylated nucleotide, etc.), for example, A; but not be limited thereto.

As used herein, the term "deletion, substitution, or insertion of PDK gene" may refer to the deletion, substitution, or insertion of PDK1 gene as described above; the deletion, substitution, or insertion of PDK2 gene as described above; the deletion, substitution, or insertion of PDK3 gene, as described above; or a combination of at least two selected therefrom.

The step of inactivating PDK gene may be carried out by deletion of an entire PDK gene, deletion or substitution of a part of PDK gene, insertion of at least one nucleotide into PDK gene, and/or treatment with a PDK gene expression inhibitor, in a genome of host cell, as described above. For example, the step of inactivating PDK gene may be performed by:

1) deletion of an entire PDK gene,
2) deletion of about 1 to about 100 consecutive nucleotides of PDK gene or substitution of about 1 to about 100 consecutive nucleotides of PDK gene with different nucleotide from that of wild-type PDK gene,
3) insertion of about 1 to about 100 nucleotides in total, each of which is independently selected from A, T (or U), G, C, and modified nucleotides, into coding region, non-coding region, and/or expression (transcription) regulatory region of PDK gene,
4) treatment with a PDK gene expression inhibitor, or
5) a combination thereof.

The deletion of an entire PDK gene, deletion or substitution of a part of PDK gene, insertion of at least one nucleotide into PDK gene, and/or treatment of a PDK gene expression inhibitor, in a genome of host cell may be carried out by any general method known to the relevant field.

For example, the deletion of an entire PDK gene, deletion or substitution of a part of PDK gene, and/or insertion of at least one nucleotide into PDK gene may be carried out using a recombinant vector for inactivation of PDK gene.

The recombinant vector for inactivation of PDK gene may be a vector capable of inducing the deletion of an entire PDK gene, deletion or substitution of a part of PDK gene, and/or insertion of at least one nucleotide into PDK gene, in a genome of a host cell, as described above.

For example, the recombinant vector for inactivation of PDK gene may comprise
i) a polynucleotide fragment ("targeting polynucleotide fragment"; e.g., an RNA fragment, etc.) that targets (e.g., specifically binds to or comprises a complementary sequence to) a certain gene ("target gene") to be inactivated or a certain region ("target region") of the target gene, and
ii) a polynucleotide encoding a nuclease (e.g., Cas proteins such as Cas9, etc.) that cleaves a specific site within the target gene or the target region.

The targeting polynucleotide fragment and the nuclease may be comprised together in one vector together or separately in different vectors from each other. For example, the recombinant vector for inactivation of PDK gene may comprise:
i) an RNA fragment of about 5 to about 100 bp (e.g., about 5 to about 50 bp, about 10 to about 50 bp, about 20 to about 50 bp, about 5 to about 40 bp, about 10 to about 40 bp, about 20 to about 40 bp, about 5 to about 30 bp, about 10 to about 30 bp, or 20 to 30 bp) comprising a complementary sequence to the target region in PDK gene, and
ii) a polynucleotide encoding Cas9 protein,
wherein the RNA fragment and Cas9 gene may be comprised together in one vector or separately in different vectors from each other.

A recombinant vector further comprising a gene ("gene of interest") encoding a polypeptide of interest may be used as an expression vector for expressing the polypeptide of interest in a cell.

The recombinant vector may be constructed by any method known to the relevant field.

In the recombinant vector for inactivation of PDK gene and/or the recombinant vector for expressing the polypeptide of interest, the polynucleotide for inactivation of PDK gene and/or the gene of interest may be operatively linked to general gene expression (transcription) regulatory elements, such as a promoter, transcription terminator, and the like. The term "operatively linked" is intended to pertain to a functional linkage between a gene of interest and an expression regulatory element (for example, a promoter sequence) so that the expression of the gene of interest is controlled by the regulatory element. For instance, when the expression regulatory element such as a promoter is "operatively linked" to the gene of interest, it can control the transcription and/or translation of the gene of interest. In the recombinant vector, the expression regulatory element may be linked to 5'-end of a gene of interest, so that it can be operatively linked thereto.

The promoter is one of transcription regulatory elements and may be a polynucleotide fragment of about 100 to about 2000 bp or about 100 to 1000 bp, but not be limited thereto. In this disclosure, any promoter capable of regulating the initiation of transcription of a gene in a cell for example, a virus cell, a bacterial cell, or a eukaryotic cell (e.g., an insect cell, a plant cell, or an animal cell, such as a mammalian cell) can be used with no limitation. For example, the promoter may be at least one selected from the group consisting of promoters of prokaryotic cells or mammalian viruses, such as CMV promoter (cytomegalovirus promoter; e.g., human CMV (human cytomegalo virus; hCMV) promoter), SV40 promoter, adenovirus promoter (major late promoter), pLλ promoter, trp promoter, lac promoter, tac promoter, T7 promoter, vaccinia virus 7.5K promoter, HSV tk promoter, and the like, and promoters of animal cells, such as metallothionein promoter, ubiquitin promoter, beta-actin promoter, and the like, but not be limited thereto.

The term "vector" refers to any means for expressing a target gene in a host cell. A vector may comprise elements necessary for expressing a gene of interest, such as a replication origin, a promoter, an operator, a terminator, and the like. In addition, a vector may further comprise at least one selected from the group consisting of an enzyme recognition site (e.g., a recognition (restriction) site of a restriction enzyme) for introducing a foreign gene into a genome of a host cell, a selection marker for confirming a successful introduction of the vector into a host cell, a ribosome binding site (RBS) for translation to a protein, an internal ribosome entry site (IRES), and the like (see FIG. 1). A vector may be genetically engineered so as to comprise the fusion polypeptide as a promoter. A vector may further comprise transcription control sequences (e.g., an enhancer) in addition to a promoter.

The terminator may be a polyadenylation sequence (pA). The origin of replication may be an f1 origin of replication, an SV40 origin of replication, a pMB1 origin of replication, an adeno origin of replication, an AAV origin of replication, or a BBV origin of replication, and any combination thereof.

The selection marker may refer to a gene for confirming whether or not the recombinant vector is successfully introduced into a host cell or establishing a stable recombinant cell comprising the recombinant vector. For example, the selection marker may be at least one selected from the group consisting of drug-resistant genes (e.g., an antibiotic-resistant gene), metabolism-related genes, gene-amplifying genes, and the like. The selection marker should not affect the expression efficiency of the vector. In an embodiment, the selection marker may be selected from any drug-resistant genes (e.g., an antibiotic-resistant gene) and metabolism-related genes, which is generally used for a recombinant vector. For example, the selection marker may be at least one selected from the group consisting of an ampicillin-resistant gene, a tetracyclin-resistant gene, a kanamycin-resistant gene, a chloroamphenicol-resistant gene, a streptomycin-resistant gene, a neomycin-resistant gene, a zeocin-resistant gene, a puromycin-resistant gene, a thymidine kinase (TK) gene, a dihydrofolate reductase (DHFR) gene, a glutamine synthetase (GS) gene, and the like, but not be limited thereto. The vector to be used for constructing a recombinant vector may be exemplified by a plasmid vector, a cosmid vector, or a viral vector such as a bacteriophage vector, adenovirus vector, retrovirus vector, and an adeno-related virus vector. The recombinant vector may be constructed from, but not limited to, well-known plasmids (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), phages (for example, λgt4λB, λ-Charon, λΔz1, M13, etc.) or viruses (for example, SV40, etc.) by manipulation.

The recombinant cell may be established by introducing an inactivated PDK gene, as described above, into a host cell; that is, by inactivating PDK gene in genome of a host cell.

The host cell for preparing the recombinant cell may be any prokaryotic cell (e.g., E. coli, etc.) or any animal cell (e.g., any mammalian cell) comprising PDK gene in its genome, wherein a promoter comprised in a recombinant vector can operate (i.e., initiate transcription) and an expression of a gene of interest is allowed. For example, the host cell may be a mammalian cell selected from the group consisting of a mouse cell (e.g., COP, L, C127, Sp2/0, NS-0, NS-1, At20, NIH3T3, etc.), a rat cell (e.g., PC12, PC12h, GH3, MtT, etc.), a hamster cell (e.g., BHK, CHO, GS (glutamine synthetase) gene deficient CHO, DHFR (dihydrofolate reductase) gene deficient CHO, etc.), a monkey cell (e.g., COS1, COS3, COST, CV1, Vero, etc.), a human cell (e.g., Hela, HEK-293, PER C6 cell derived from retinal tissue, a cell derived from diploid fibroblast, myeloma cell, HepG2, etc.), and the like, but not limited thereto. The host cell may be isolated (separated) from a living body. In an embodiment, the PDK gene is an endogenous gene in a host cell as described above.

The introduction of a recombinant vector into a host cell may be carried out by any method known in the relevant art. The genetic introduction may be performed using, but not limited to, microinjection, calcium phosphate precipitation, electroporation, liposome-mediated transfection, or particle bombardment.

A transfected host cell, wherein a recombinant vector is successfully introduced, may be selected by any conventional method using a selection marker. For example, when the selection marker is a gene resistant to a certain antibiotic as described above, the host cells may be grown in the presence of the antibiotic in a medium to select a transfected cell.

When a polypeptide (e.g., an antibody, etc.) of interest has an effect of preventing, treating, improving, and/or ameliorating a disease and/or a pathologic condition, an embodiment provides a pharmaceutical composition comprising at least one selected from the group consisting of a recombinant vector for expressing a gene encoding the polypeptide of interest, a recombinant cell comprising the gene encoding the polypeptide of interest, and a culture (in a cell-containing or cell-free form) of the recombinant cell.

Another embodiment provides a method of producing a polypeptide of interest using the recombinant vector or the recombinant cell. For example, the method of producing a polypeptide of interest may comprise expressing a gene encoding a polypeptide of interest in the recombinant cell. The step of expressing a gene may be performed in vitro. The step of expressing a gene may comprise culturing the recombinant cell in a medium for the cell and under conditions allowing expression of the gene in the cell, wherein the medium and conditions may be clear to the relevant art. The recombinant cell may be a cell comprising inactivated PDK gene (endogenous gene) and a gene encoding a polypeptide of interest (foreign gene).

In addition, the production method may further comprise harvesting (obtaining or separating) the polypeptide of interest from the expressing or culturing product, after the step of expressing or culturing. The step of harvesting the polypeptide of interest may be performed by separating the polypeptide from the recombinant cell, a lysate thereof, and/or a culture media (in case the polypeptide is secreted to a medium). The method of producing may further comprise an additional step, such as a step of purification and/or modification, so that the harvested polypeptide can have a desired quality and/or purity.

As used herein, the term "polypeptide" refers to a molecule covering a polymer of amino acids which are linked to one another through peptide bond(s). The polypeptide may a polypeptide in any length; for example, the polypeptide may be a protein (e.g., comprising about 50 or more amino acids) or a peptide (e.g., comprising about 2 to 49 amino acids).

The term "polypeptide of interest" may refer to a protein or a peptide having a desired activity (e.g., an activity of treating, preventing, and/or ameliorating a certain disease or symptom, and/or replacing a substance necessary in a living body) in a living body or a cell. The polypeptide of interest may be endogenous or exogenous (from identical or different species). For example, the polypeptide of interest may be at least one selected from the group consisting of a protein or peptide having an enzymatic activity (e.g., a protease, a kinase, a phosphatase, etc.), a receptor protein or peptide, a transporter protein or peptide, a microbiocidal and/or endotoxin-binding polypeptide, a structural protein or peptide, an immunoglobulin, a toxin, an antibiotic, a hormone, a growth factor, a vaccine, and the like. The polypeptide of interest or the gene of interest may be intrinsic (i.e., originally present in a host cell) or extrinsic (i.e., introduced from out of a host cell), and in case the polypeptide or gene is extrinsic, it may be introduced from the same species with or different species from the host cell.

In an embodiment, the polypeptide of interest may be at least one selected from the group consisting of a hormone, a cytokine, a tissue plasminogen activator, an immunoglobulin (e.g., an antibody or an antigen-binding fragment thereof or a variant thereof), and the like. The immunoglobulin (also refers to an antibody) may be any isotype (e.g., IgA, IgD, IgG, IgM or IgE), for example, IgG molecule (e.g., IgG1, IgG2, IgG3, or IgG4). The antigen-binding fragment refers to an antibody fragment possessing an antigen binding ability of the antibody, and may be comprise or consist essentially of at least about 20 amino acids, for example, at least about 100 amino acids. The antigen-binding fragment may be any fragment containing an antigen-binding region, and for example, it may be at least one selected from the group consisting of CDRs (complementarity determining regions), a Fab fragment, a Fab' fragment, a F(ab)2 fragment, a F(ab')2 fragment, a Fv fragment, a scFv fragment, a (scFv)2 fragment, a scFv-Fc fragment, a multibody containing various antigen-binding domains (e.g., a diabody, a triabody, a tetrabody, etc.), a single-domain antibody, an affibody, and the like. The variant of an antibody refers to a derivative of an antibody or an antibody fragment, which has an amino acid sequence modified from the amino acid sequence of an original antibody, with maintaining an antigen-binding ability of the original antibody. The antibody and/or antigen-binding fragment may be, but not limited to, animal antibodies (e.g., mouse-derived antibodies), chimeric antibodies (e.g., mouse-human chimeric antibodies), humanized antibodies, or human antibodies. The antibody or antigen-binding fragment may be isolated from a living body or non-naturally occurring (e.g., being synthetic or recombinant). The antibody may be monoclonal. When the polypeptide of interest is an antibody or antigen-binding fragment, a gene encoding a heavy chain and a gene encoding a light chain may be carried together in one vector, or separately in different vectors. Alternatively, the polypeptide of interest may be at least one selected from the group consisting of insulin, human growth hormone (hGH), various growth factors, such as insulin-like growth factor, epidermal growth factor (EGF), vascular endothelial growth factor (VEGF), and the like, various receptors, tissue plasminogen activator (tPA), erythropoietin (EPO), cytokines (e.g., interleukin such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, and the like), interferon (IFN)-alpha, IFN-beta, IFN-gamma, IFN-omega or IFN-tau, tumor necrosis factors (TNF) such as TNF-alpha, TNF-beta or TNF-gamma, TRAIL, G-CSF, GM-CSF, M-CSF, MCP-1, and the like. The polypeptide of interest and/or vector encoding same may further comprise a sequence that assists in harvesting the polypeptide from the cell, e.g., a signal sequence or the like.

In an embodiment, the polypeptide of interest may be an anti-c-Met antibody or an antigen-binding fragment thereof. In one embodiment, the anti-c-Met antibody may any of those described in Korean Patent Publication No. 2011-0047698, U.S. Pat. No. 8,563,696 B2, or US Patent Publication No. 2013-0089542 A1, the entire disclosures of which are incorporated in by reference.

This disclosure may provide a recombinant vector for an animal cell (e.g., a mammalian cell) for high expression of a therapeutic protein or antibody, which can be useful in mass-production of various therapeutic proteins.

EXAMPLES

Hereafter, the present invention will be described in detail by examples. The following examples are intended merely to illustrate the invention and are not construed to restrict the invention.

Example 1: Preparation of PDK-Inactivated CHO Cell

PDK1/2/3 gene in a genome of CHO cell was inactivated by partial modification (partial deleted or insertion) using Crispr-cas9 system (ToolGen RNA-Guided Endonucleases (RGEN) system).

Figure 2:
FIG. 2 is a cleavage map of pRGEN_CHO-PDK1_U6_SG vector.
Figure 3:
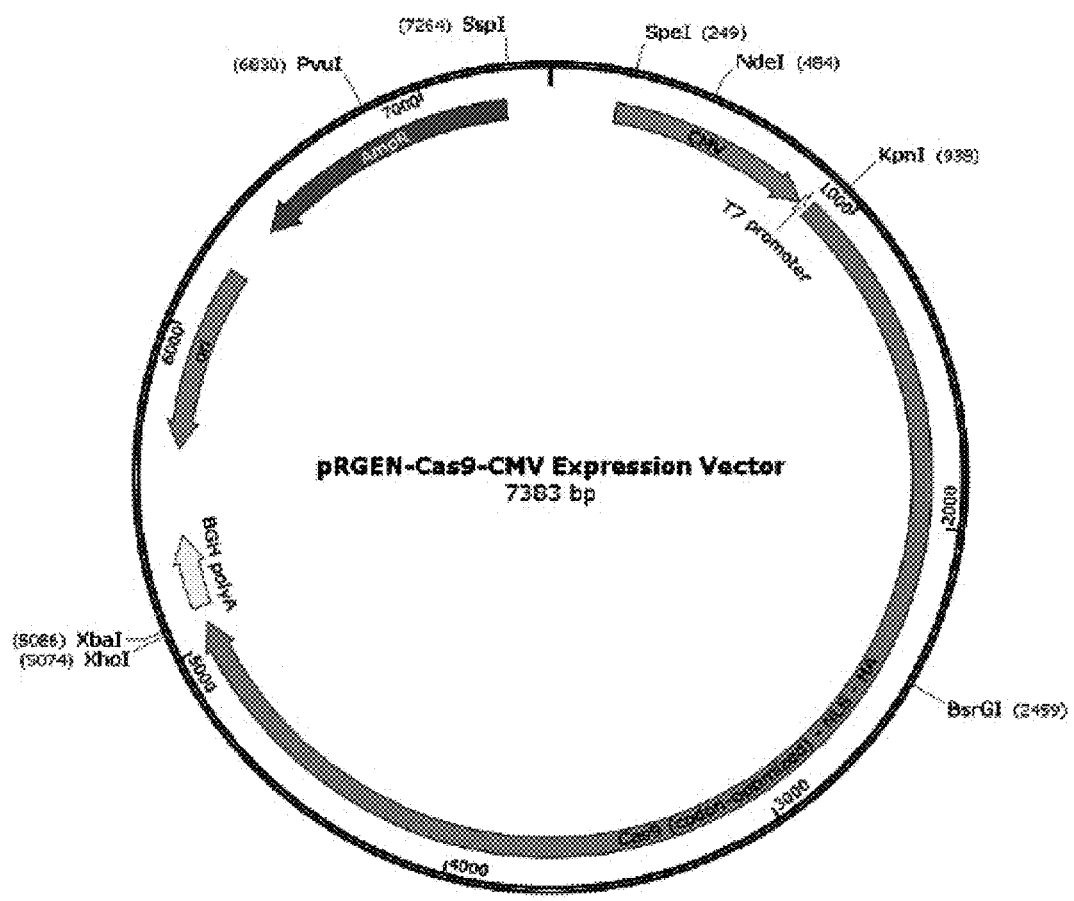
FIG. 3 is a cleavage map of pRGEN_Cas9_CMV expression vector.

Specifically, PDK1 gene was inactivated by modification of a part of PDK gene by following method. pRGEN_CHO-PDK1_U6_G vector (ToolGen; SEQ ID NO: 21; selection marker: Ampicillin; promoter: U6, SalI/XbaI: 2052/438 bp; FIG. 2) targeting a region having the nucleotide sequence (caatgatgtcattccaaccatgg (23 bp); SEQ ID NO: 12; sgRNA (single guide RNA) direction: up) from $219^{th}$ to $241^{st}$ positions of PDK1 gene (SEQ ID NO: 6) and pRGEN_Cas9_CMV expression vector (ToolGen; selection marker: Ampicillin; promoter: CMV, KpnI/XhoI: 4136/3247 bp; FIG. 3) for expression of Cas9 were provided. As host cell, CHOK1SV GS Knockout (KO) host cell line (Sigma, CHOZN_GS−/− ZFN-modified CHO cell line, #CHOGS, glutamine synthetase (GS) gene knockout; hereinafter, "GSKO cell") was provided. The two vectors were transferred (transfected) into the GSKO cells ($5*10^6$ cells) in a DNA total amount of 10 μl (pRGEN_CHO-PDK1_U6_SG: pRGEN_Cas9_CMV=1:1) using Amaxa nucleofector sf kit (catalog # V4XC-2024), to produce clones wherein a modified (inactivated) PDK gene with partial deletion from SEQ ID NO: 6 (see FIG. 6 and Table 3).

Figure 4:
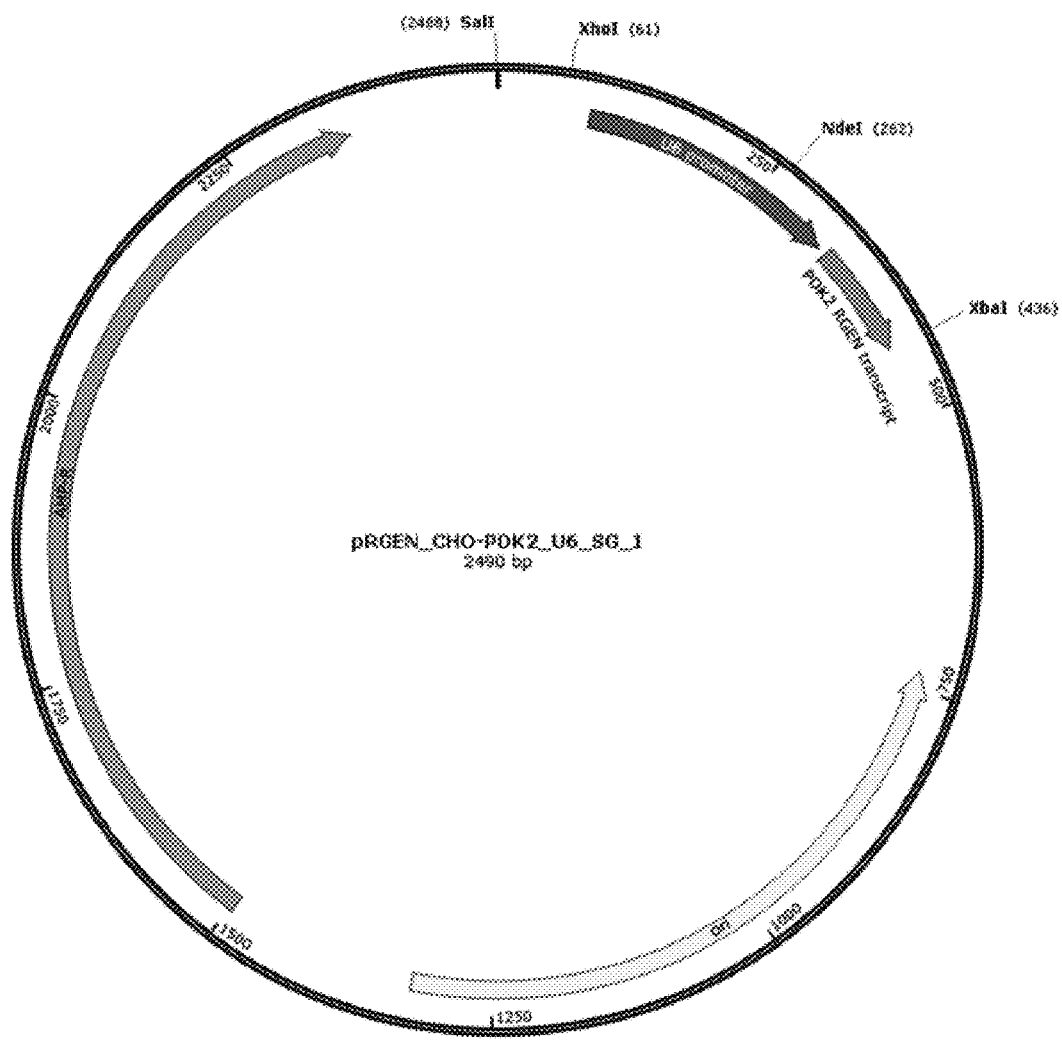
FIG. 4 is a cleavage map of pRGEN_CHO-PDK2_U6_SG vector.
Figure 5:
FIG. 5 is a cleavage map of pRGEN_CHO-PDK3_U6_SG vector.

In the cases of PDK2 and PDK3 genes, partial modifications (deletions) were conducted referring to the above method, thereby being inactivated. For a partial modification of PDK2 gene, pRGEN_CHO-PDK2_U6_SG vector (ToolGen; SEQ ID NO: 22; selection marker: Ampicillin; promoter: U6, SalI/XbaI: 2052/438 bp; FIG. 4) targeting a region having the nucleotide sequence (cctgtgcgcctggccaacatcat (23 bp); SEQ ID NO: 15; sgRNA direction: down) from $172^{nd}$ to $194^{th}$ positions of PDK2 gene (SEQ ID NO: 8) and pRGEN_Cas9_CMV expression vector were used. For a partial modification of PDK3 gene, pRGEN_CHO-PDK3_U6_SG vector (ToolGen; SEQ ID NO: 23; selection marker: Ampicillin; promoter: U6, SalI/XbaI: 2052/438 bp; FIG. 5) targeting a region having the nucleotide sequence (ccaaacagatcgagcgctactcc (23 bp); SEQ ID NO: 19; sgRNA direction: down) from $38^{th}$ to $60^{th}$ positions of PDK3 gene (SEQ ID NO: 10) and pRGEN_Cas9_CMV expression vector were used. As the results, clones having partial deletion of PDK2 gene (2-8mPDK2_m1: 177-183 region (gcgcctg) removed; 2-8mPDK2_m2: 176-183 region (tgcgcctg) removed) and clones having nucleotide insertion into PDK2 gene (2-33 mPDK2: nucleotides "cc" were inserted between $179^{th}$ and $180^{th}$ positions), and clones having nucleotide insertion into PDK3 gene (2-8mPDK3: nucleotide "a" was inserted between $44^{th}$ and $45^{th}$ positions of PDK3 gene (SEQ ID NO: 10)) were obtained (see Tables 4 and 5, and FIGS. 7 to 9).

The obtained clones were subjected to PCR using gDNA as a template. The gDNA was obtained using QIAamp DNA mini kti (cat #51306; Qiagen). The PCR was performed using primers listed in Table 1 and Phusion (M0530, NEB) under the conditions of Table 2, to generate PCR products.

TABLE 1

| PDK1 Forward | GGGAAACCCTTAACACTGCTC (SEQ ID NO: 30) |

TABLE 1-continued

| | | |
|---|---|---|
| PDK1 reverse | ATC AAA AGC GAA AAG CCA AA (SEQ ID NO: 31) | |
| PDK2 forward | TTGAGGTGACTTAGGCCAGAA (SEQ ID NO: 32) | |
| PDK2 reverse | GCCAAGGGTTACTGCTGACA (SEQ ID NO: 33) | |
| PDK3 forward | ACTGCCTCTGGTGCTTGTTT (SEQ ID NO: 34) | |
| PDK3 reverse | TGAGAGTCCTTGGAGGAAGC (SEQ ID NO: 35) | |

TABLE 2

| | Temperature (° C.) | Time | Cycle |
|---|---|---|---|
| Pre | 94 | 5 min | |
| Cycle | 94 | 30 sec | 35 cycles |
| | 68 | 30 sec | |
| Post | 72 | 10 min | |

The obtained PCR products were cloned using pJET PCR cloning kit (thermo scientific, K1231), transformed into top 10 competent cell (Invitrogen, C4040-10), and then, DNAs obtained from 10 colonies were subjected to sequence analysis, to confirm the partial modification of PDK gene.

Figure 7:
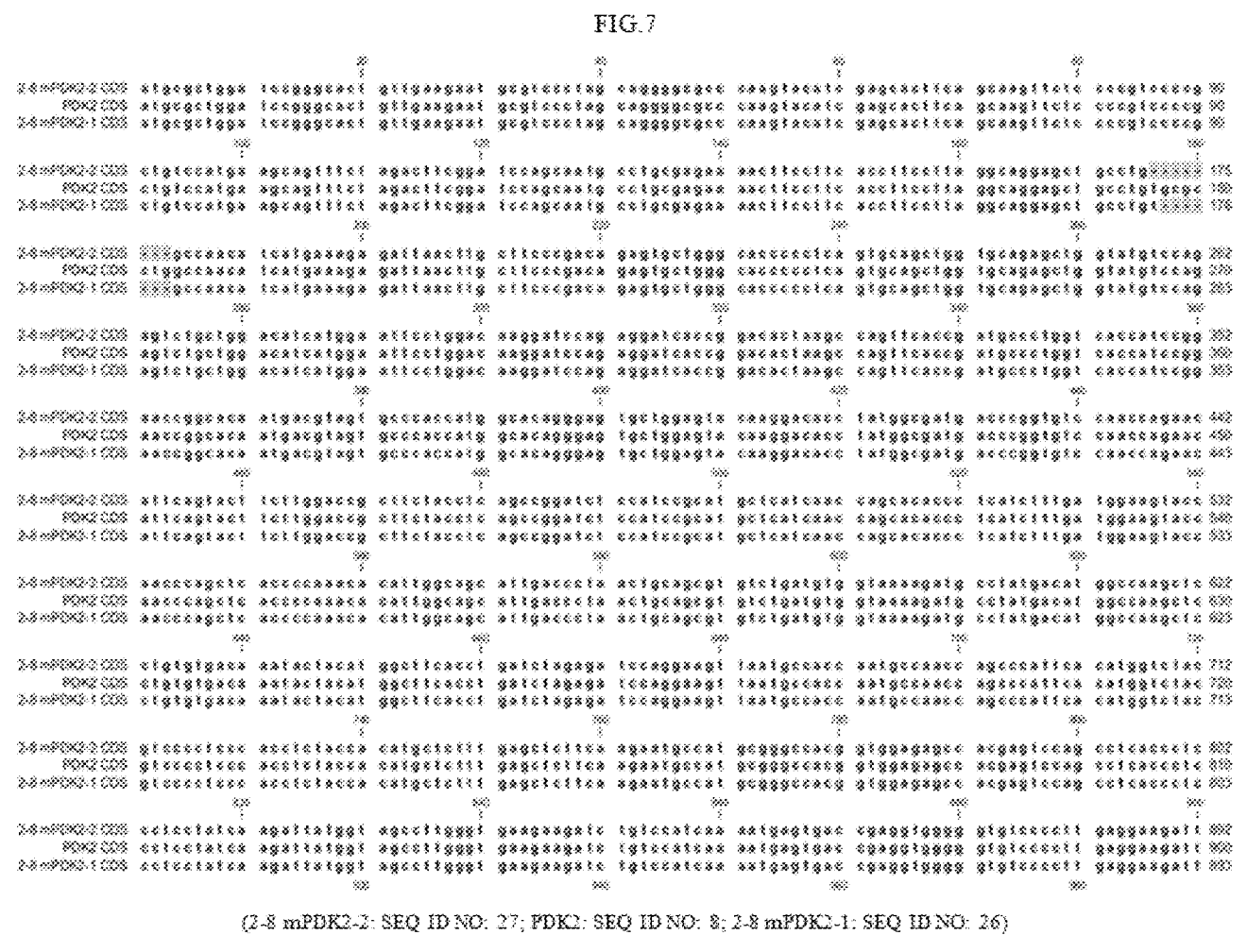
Figure 8:
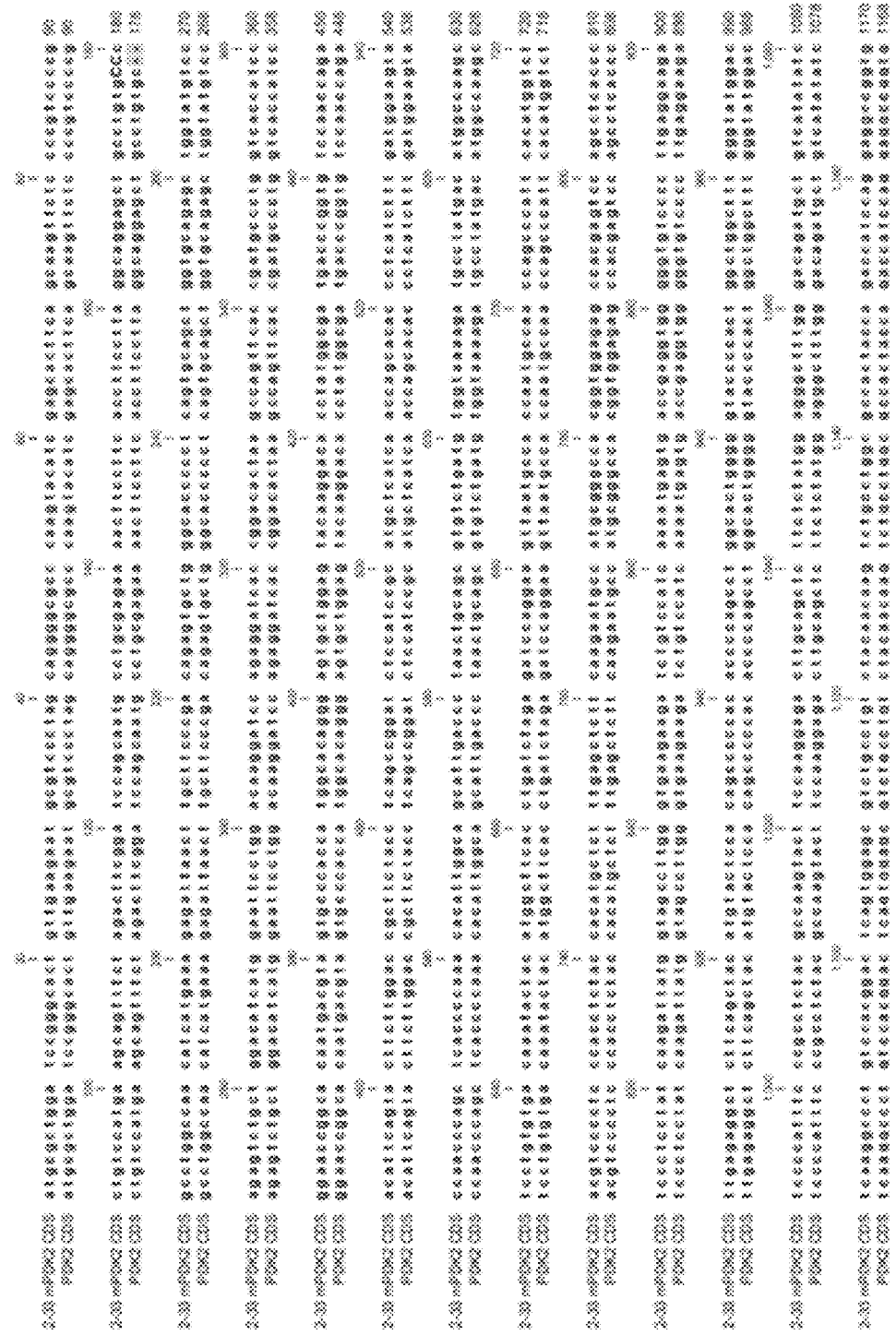
FIG. 8 shows genetic information of a clone having a partial deletion of PDK2 gene.
Figure 9:
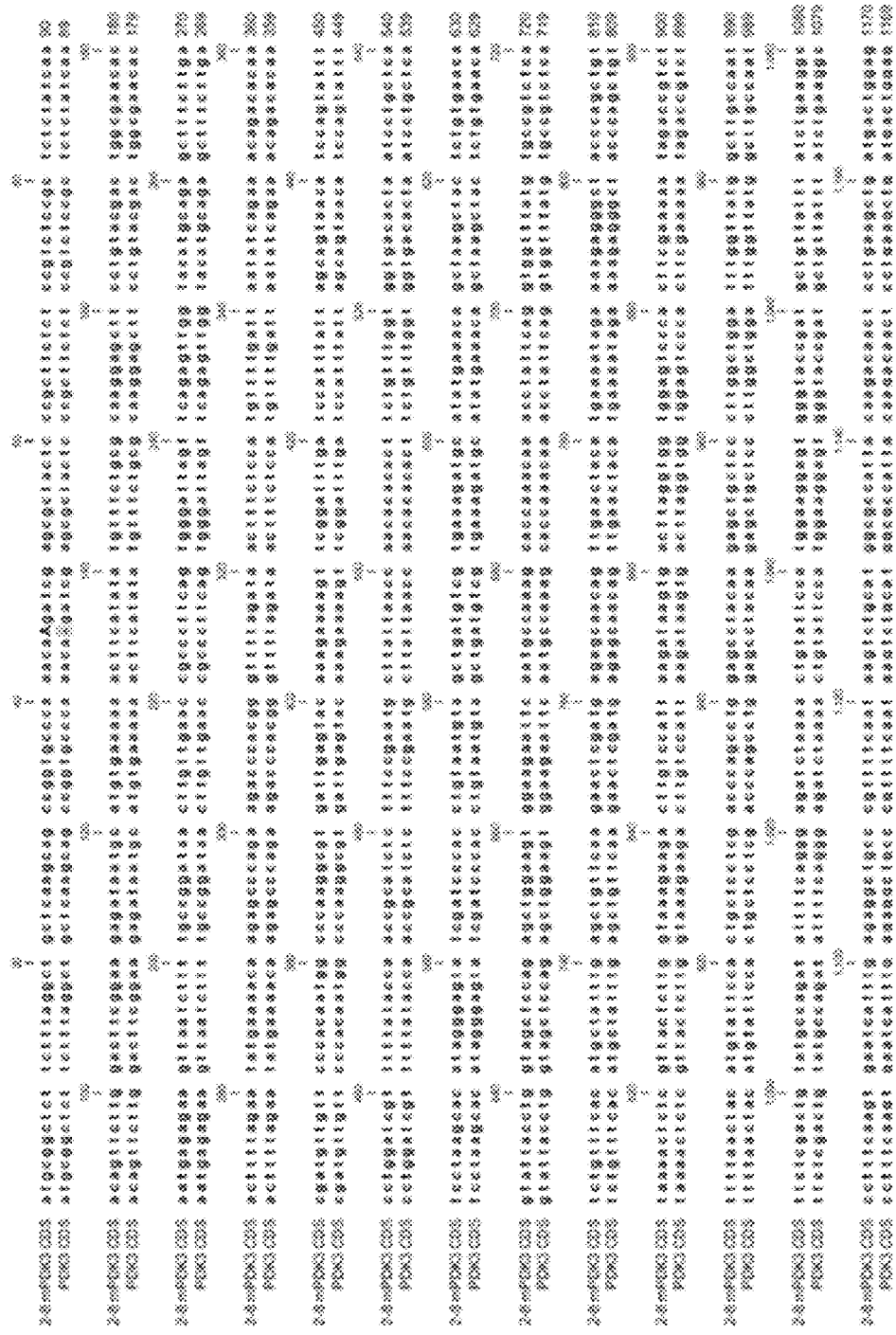
FIG. 9 shows genetic information of a clone having a partial deletion of PDK3 gene.

The modification regions of clones and amino acid sequences of polypeptides generated from the modified clones were summarized in Tables 3-5, and nucleotide sequence information of clones was shown in FIGS. 6-9 (FIG. 6: partial deletion of PDK1 gene, FIGS. 7 and 8: partial deletion of PDK2 gene, and FIG. 9: partial deletion of PDK3 gene).

TABLE 3

Clones having partial modification (deletion) of PDK1 gene

| Clone | Gene deletion region (based on SEQ ID NO: 6) | Amino acid sequence encoded by gene having partial deletion |
|---|---|---|
| 2-8mPDK1_M1 | 238-241 region (atgg) | MFLRQELPVRLANIMKEIS LLPDNLLRTPSVQLVQSWY IQSLQELLDFKDKSAEDAK TIYEFTDTVIRIRNRHNDV IPTPRV (SEQ ID NO: 13; gene with partial deletion: SEQ ID NO: 24) |
| 2-8mPDK1_M2 | 235-238 region (acca) | MFLRQELPVRLANIMKEIS LLPDNLLRTPSVQLVQSWY IQSLQELLDFKDKSAEDAK TIYEFTDTVIRIRNRHNDV IPWPRV (SEQ ID NO: 14; gene with partial deletion: SEQ ID NO: 25) |

TABLE 3-continued

Clones having partial modification (deletion) of PDK1 gene

| Clone | Gene deletion region (based on SEQ ID NO: 6) | Amino acid sequence encoded by gene having partial deletion |
|---|---|---|
| 2-33mPDK1 | 238-241 region (atgg) | MFLRQELPVRLANIMKEIS LLPDNLLRTPSVQLVQSWY IQSLQELLDFKDKSAEDAK TIYEFTDTVIRIRNRHNDV IPTPRV (SEQ ID NO: 13; gene with partial deletion: SEQ ID NO: 24) |
| 1-21mPDK1 | 238-241 region (atgg) | MFLRQELPVRLANIMKEIS LLPDNLLRTPSVQLVQWYI QSLQELLDFKDKSAEDAKT IYEFTDTVIRIRNRHNDVI PTPRV (SEQ ID NO: 13; gene with partial deletion: SEQ ID NO: 24) |
| 2-10mPDK1 | Wild type/ 238-241 region (atgg) | Heterologous WT/M1 |
| 1-4mPDK1 | | the same with 2-10mPDK1 |

TABLE 4

Clones having partial modification (deletion or insertion) of PDK2 gene

| Clone | Gene modification region (based on SEQ ID NO: 8) | Amino acid sequence encoded by gene having partial modification |
|---|---|---|
| 2-8mPDK2_m1 | 177-183 region (gcgcctg): deletion | MRWIRALLKNASLAGAPK YIEHFSKFSPSPLSMKQF LDFGSSNACEKTSFTFLR QELPVPTS (SEQ ID NO: 16; gene with partial deletion: SEQ ID NO: 26) |
| 2-8mPDK2_m2 | 176-183 region (tgcgcctg): deletion | MRWIRALLKNASLAGAPK YIEHFSKFSPSPLSMKQF LDFGSSNACEKTSFTFLR QELPGQHHERD (SEQ ID NO: 17; gene with partial deletion: SEQ ID NO: 27) |
| 2-33 mPDK2 | Insertion of 'cc' between 179$^{th}$ and 180$^{th}$ nucleotides | MRWIRALLKNASLAGAPK YIEHFSKFSPSPLSMKQF LDFGSSNACEKTSFTFLR QELPVPAWPTS (SEQ ID NO: 18; gene with partial modification: SEQ ID NO: 28) |

TABLE 5

Clones having partial modification (insertion) of PDK3 gene

| Clone | Gene modification region (based on SEQ ID NO: 10) | Amino acid sequence encoded by gene having partial modification |
|---|---|---|
| 2-8mPDK3 | Insertion of "a" between 44th and 45th nucleotides | MRLFFRLLKQPVPKQDRALLPL LSVSALYQTVLGLRKR (SEQ ID NO: 20; gene with partial deletion: SEQ ID NO: 29) |

TABLE 6

Types of partial modification of PDK gene introduced in each clone

| Clone | Types of partial modification of PDK gene introduced in each clone |
|---|---|
| 2-8 | Comprising partial deletions of PDK1 gene and PDK2 gene and insertion into PDK3 gene |
| 2-10 | Comprising partial deletion of PDK1 gene |
| 1-31 | Comprising partial deletion of PDK1 gene |
| 1-21 | Comprising partial deletion of PDK1 gene |
| 1-4 | Comprising partial deletion of PDK1 gene |
| 2-33 | Comprising partial deletion of PDK1 gene and insertion into PDK2 gene |

Among the above obtained clones, a cell with partial deletions of PDK1 gene and PDK2 gene and insertion into PDK3 gene (corresponding to 2-8 clone) was deposited with the Korean Cell Line Research Foundation, an international depository authority located at Yungun-Dong, Jongno-Gu, Seoul, Korea, on Sep. 3, 2014, with Accession No. KCLRF-BP-00328.

Example 2: Preparation of Cells Producing a Polypeptide of Interest

Figure 10:
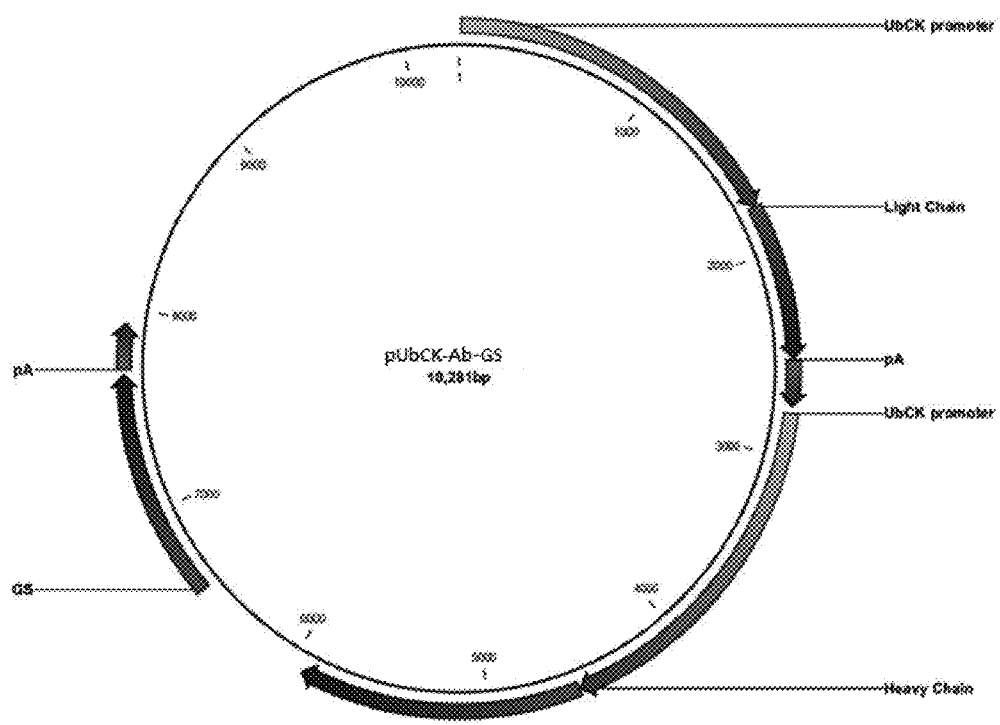
FIG. 10 is a cleavage map of antibody producing vector pUbCK-Ab-GS.

The cells with partial modification of PDK1 gene, PDK2 gene, and/or PDK3 gene selected in Example 1 were transfected with an antibody producing vector referring to the method of Example 1. The antibody producing vector was constructed so as to comprise the structure of FIG. 10 (pUbCK-Ab-GS; SEQ ID NO: 5), which includes a heavy chain gene (SEQ ID NO: 2) encoding a heavy chain (SEQ ID NO: 1) and a light chain gene (SEQ ID NO: 4) encoding a light chain (SEQ ID NO: 3) of anti-c-Met antibody (Ab). After transfection, the cells were subjected to glutamine negative selection in EX-CELL CD CHO Fusion medium (sigma, 14365C) supplemented with 1×GSEM supplement (sigma G9785) until the cell viability is 90% or more, to select recombinant cells comprising gene encoding the anti-c-Met antibody where PDK gene is partially modified.

Example 3: Antibody Productivity, Cell Growth Rate and Change in Metabolites Each of the selected cells in Example 2 was added to EX-CELL CD CHO Fusion medium (sigma, 14365C) supplemented with 1×GSEM supplement (sigma G9785) at the concentration of $5*10^5$ cell/ml, and 30 ml of the mixture of cell and medium was subjected to a small scale batch culture for 7 days.

At Day0 (D0), D3, D5, or D7 after culture, viable cell density (VCD) and cell viability were measured using cedex automated cell counter (Roche), and antibody productivity was measured using Octet protein A sensor (Fortebio).

Figure 11:
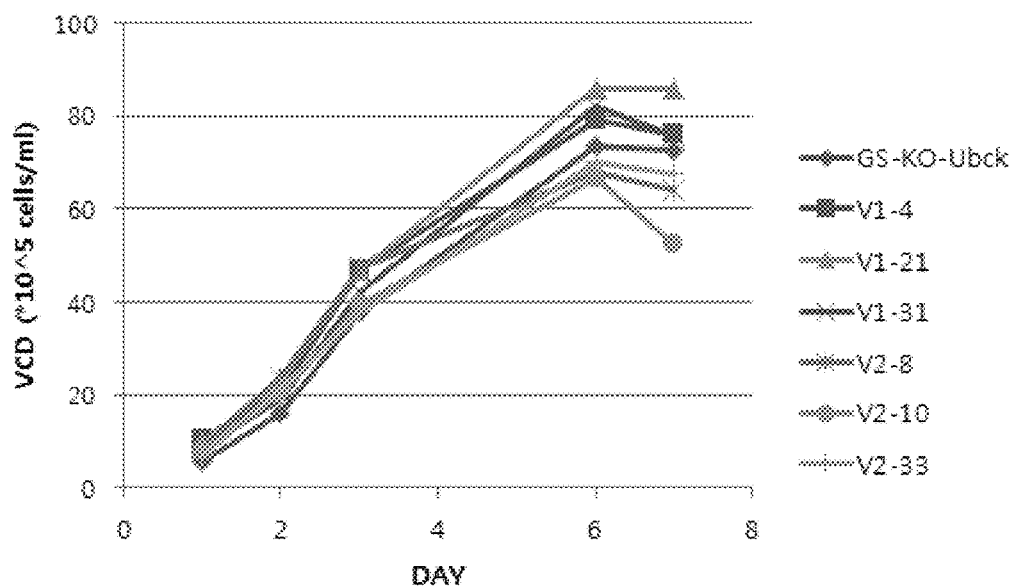
FIG. 11 is a graph showing viable cell density (VOD) of clones having a partial deletion of PDK gene.
Figure 12:
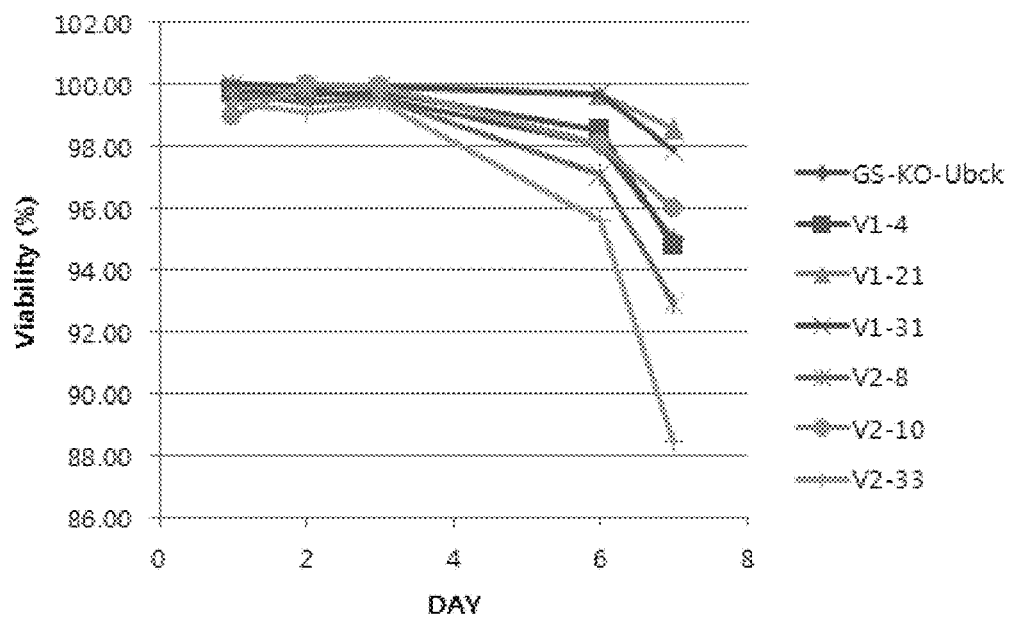
FIG. 12 is a graph showing viability of clones having a partial deletion of PDK gene.
Figure 13:
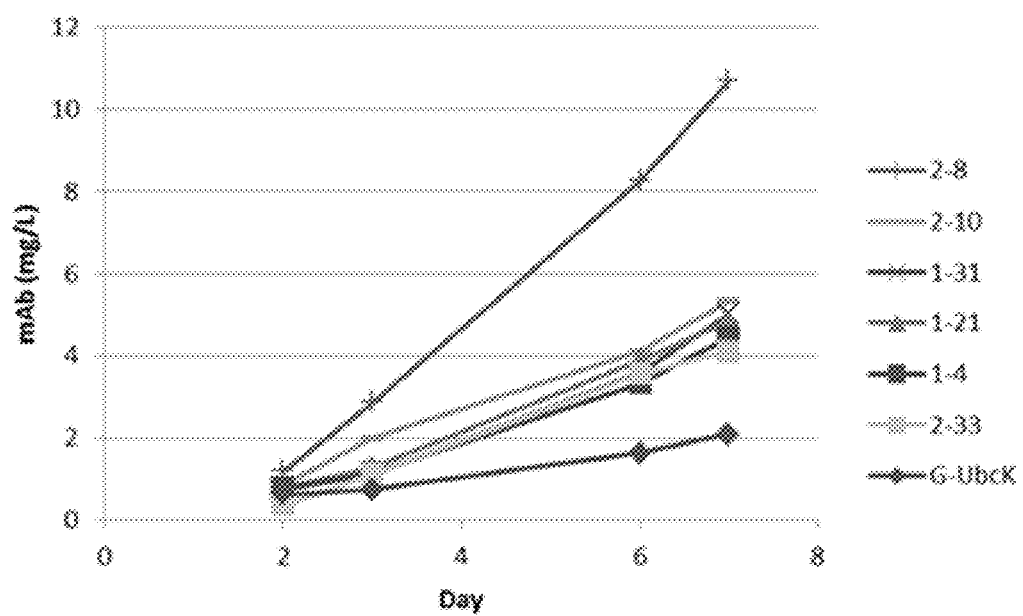
FIG. 13 is a graph showing antibody production of clones having a partial deletion of PDK gene.

The obtained results were shown in FIG. 11 (VOD), FIG. 12 (Viability), and FIG. 13 (antibody productivity). The antibody productivity at D7 was summarized in Table 7. For comparison, a cell (control) which is CHOK1SV GS Knockout (KO) host cell line (Sigma) having no PDK gene modification and transfected with the antibody producing vector (FIG. 10) described in Example 2 was subjected to the same tests as above ("GSKO-UbcK").

TABLE 7

| Clone | Ab (mg/L) |
|---|---|
| 2-8 | 10.7 |
| 2-10 | 5.34 |
| 1-31 | 5 |
| 1-21 | 4.84 |
| 1-4 | 4.45 |
| 2-33 | 4.1 |
| GSKO-UbcK | 2.1 |

As shown in FIGS. 11 to 13 and Table 7, the clones having partial modification of PDK gene show similar level of VOD and viability and at least 2-fold increased antibody productivity, compared with the control (with no modification of PDK gene).

Example 4: Purification of Anti-c-Met Antibody Produced in CHO Cell with Partial Modification of PDK Gene Anti-c-Met antibodies produced in a PDK-modified cell, 2-8 clone, and control cell were purified using protein A affinity column.

TABLE 8

| Items | GSKO (with no modification of PDK)_Ab | PDK(with modification of PDK)_Ab |
|---|---|---|
| | Antibody after Protein A purification | |
| A280 (by nanodrop) | About 0.5 mg/mL | About 1.0 mg/mL |
| SEC-HPLC | 99% | 99% |
| SDS-PAGE | The same with the Ab | The same with the Ab |

As shown in Table 8, through SEC-HPLC and SDS-PAGE, it was confirmed that antibodies produced from PDK-modified CHO cell and control cell exhibit the same expression profile to each other.

What is claimed is:

1. A recombinant cell comprising an inactivated pyruvate dehydrogenase kinase (PDK) gene,
   wherein the inactivated PDK gene comprises a deletion, substitution, or insertion mutation, such that the PDK gene cannot be expressed or cannot encode a PDK protein having normal functions.

2. The recombinant cell of claim 1, wherein the recombinant cell comprises:
   1) a deletion of the entire PDK gene,
   2) a deletion of 1 to 100 consecutive nucleotides of the PDK gene, or substitution of 1 to 100 consecutive nucleotides of the PDK gene,
   3) an insertion of 1 to 100 nucleotides into the PDK gene, or
   4) a combination thereof.

3. The recombinant cell of claim 1, wherein the recombinant cell comprises:
   a deletion of 1 to 50 consecutive nucleotides of the PDK gene;
   a substitution of 1 to 50 consecutive nucleotides of the PDK gene;
   an insertion of 1 to 50 nucleotides into the PDK gene; or
   a combination thereof.

4. The recombinant cell of claim 1, wherein the PDK gene is at least one selected from the group consisting of PDK1 gene, PDK2 gene, and PDK3 gene.

5. The recombinant cell of claim 1, comprising:
   an inactivated PDK1 gene in which 1 to 7 nucleotides from the $235^{th}$ to $241^{st}$ positions of SEQ ID NO: 6 are deleted or substituted with a different nucleotide,
   an inactivated PDK2 gene in which 1 to 20 nucleotides from the $172^{nd}$ to $194^{th}$ positions of SEQ ID NO: 8 are deleted or substituted with a different nucleotide, and/or 1 to 20 nucleotides are inserted within the region from the $172^{nd}$ to $194^{th}$ positions of SEQ ID NO: 8,
   an inactivated PDK3 gene in which 1 to 20 nucleotides are inserted within the region from the $38^{th}$ to $60^{th}$ positions of SEQ ID NO: 10, or a combination thereof.

6. The recombinant cell of claim 1, comprising:
an inactivated PDK1 gene in which the nucleotides from the 235$^{th}$ to 238$^{st}$ positions of SEQ ID NO: 6 or the 238$^{th}$ to 241$^{st}$ positions of SEQ ID NO: 6 are deleted or substituted with a different nucleotide,
an inactivated PDK2 gene in which the nucleotides from the 177$^{th}$ to 183$^{rd}$ positions of SEQ ID NO: 8 or from the 176$^{th}$ to 183$^{rd}$ positions of SEQ ID NO: 8 are deleted or substituted with a different nucleotide, or 1 to 3 nucleotides are inserted at the 180$^{th}$ position of SEQ ID NO: 8,
an inactivated PDK3 gene in which a nucleotide is inserted at the 45$^{th}$ position of SEQ ID NO: 10, or
a combination thereof.

7. The recombinant cell of claim 1, further comprising a recombinant vector encoding a polypeptide of interest.

8. The recombinant cell of claim 2, further comprising a recombinant vector encoding a polypeptide of interest.

9. The recombinant cell of claim 5, further comprising a recombinant vector encoding a polypeptide of interest.

10. The recombinant cell of claim 1, wherein the cell is a Chinese Hamster Ovary cell.

11. The recombinant cell of claim 10, wherein glutamine synthetase (GS) gene in the cell is knocked out.

12. A method of producing a polypeptide of interest, comprising expressing the recombinant vector encoding the polypeptide of interest in the recombinant cell of claim 7.

13. A method of producing a polypeptide of interest, comprising expressing the recombinant vector encoding the polypeptide of interest in the recombinant cell of claim 8.

14. A method of producing a polypeptide of interest, comprising expressing the recombinant vector encoding the polypeptide of interest in the recombinant cell of claim 9.

15. A method of preparing the recombinant cell of claim 1, the method comprising inactivating a PDK gene in a cell, wherein the inactivated PDK gene comprises a deletion, substitution, or insertion mutation, such that the PDK gene cannot be expressed or cannot encode a PDK protein having normal functions.

16. The method of claim 15, wherein the PDK gene is at least one selected from the group consisting of PDK1 gene, PDK2 gene, and PDK3 gene.

17. The method of claim 15, wherein the step of inactivating a PDK gene comprises:
 1) deleting the entire PDK gene,
 2) deleting 1 to 100 consecutive nucleotides of the PDK gene, or substituting 1 to 100 consecutive nucleotides of the PDK gene with different nucleotides,
 3) inserting 1 to 100 nucleotides into the PDK gene, or
 4) a combination thereof.

18. The method of claim 15, wherein the step of inactivating a PDK gene comprises:
 in a PDK gene comprising SEQ ID NO: 6, deleting or substituting 1 to 7 nucleotides from the 235$^{th}$ to 241$^{st}$ positions of SEQ ID NO: 6,
 in a PDK gene comprising SEQ ID NO: 8, deleting or substituting 1 to 20 nucleotides from the 172$^{nd}$ to 194$^{th}$ positions of SEQ ID NO: 8, or inserting 1 to 20 nucleotides within the region from the 172$^{nd}$ to 194$^{th}$ positions of SEQ ID NO: 8,
 in a PDK gene comprising SEQ ID NO: 10, inserting 1 to 20 nucleotides into a region from the 38$^{th}$ to 60$^{th}$ positions of SEQ ID NO: 10, or
 a combination thereof.

19. The recombinant cell of claim 1, wherein the cell comprises an inactivated PDK1 gene, PDK2 gene, and PDK3 gene.

* * * * *